(12) United States Patent
Anderson

(10) Patent No.: US 11,619,220 B1
(45) Date of Patent: Apr. 4, 2023

(54) CONTINUOUS FLOW INFUSION PUMP UTILIZING ANGULAR ALIGNED FINGERS

(71) Applicant: Wayne Richard Anderson, Eden Prairie, MN (US)

(72) Inventor: Wayne Richard Anderson, Eden Prairie, MN (US)

(*) Notice: Subject to any disclaimer, the term of this patent is extended or adjusted under 35 U.S.C. 154(b) by 0 days.

(21) Appl. No.: 17/845,236

(22) Filed: Jul. 5, 2022

(51) Int. Cl.
| | |
|---|---|
| *F04B 43/08* | (2006.01) |
| *F04B 43/12* | (2006.01) |
| *F04B 23/02* | (2006.01) |
| *A61M 39/28* | (2006.01) |
| *A61M 5/142* | (2006.01) |

(52) U.S. Cl.
CPC ....... *F04B 43/082* (2013.01); *A61M 5/14228* (2013.01); *A61M 39/281* (2013.01); *F04B 23/02* (2013.01); *F04B 43/12* (2013.01)

(58) Field of Classification Search
CPC ........ F04B 43/082; F04B 23/02; F04B 43/12; F04B 43/1223; A61M 5/14228; A61M 39/281
See application file for complete search history.

(56) References Cited

U.S. PATENT DOCUMENTS

| | | | |
|---|---|---|---|
| 4,187,057 A | 2/1980 | Xanthopoulos | |
| 4,256,437 A | 3/1981 | Brown | |
| 4,898,579 A | 2/1990 | Groshong | |
| 5,322,422 A | 6/1994 | Natwick | |
| 5,407,424 A | 4/1995 | LaFontaine | |
| 5,478,211 A | 12/1995 | Dominiak | |
| 5,522,799 A | 6/1996 | Furukawa | |
| 5,526,962 A | 6/1996 | Huggenberger | |
| 5,575,631 A * | 11/1996 | Jester ................ | A61M 5/14228 417/474 |
| 5,683,233 A * | 11/1997 | Moubayed ............. | F04B 43/12 417/474 |
| 5,718,569 A | 2/1998 | Holst | |
| 5,791,881 A * | 8/1998 | Moubayed ............ | F04B 43/082 417/474 |
| 5,904,668 A | 5/1999 | Hyman | |
| 5,924,852 A * | 7/1999 | Moubayed ............. | F04B 43/12 417/474 |
| 6,164,921 A * | 12/2000 | Moubayed ............ | F04B 43/082 417/474 |
| 7,934,912 B2 | 5/2011 | Voltenburg | |
| 8,100,675 B2 * | 1/2012 | Miyazaki ............. | F04B 43/082 417/477.6 |
| 8,303,275 B2 * | 11/2012 | Miyazaki .......... | A61M 5/14228 417/477.1 |
| 8,317,500 B2 * | 11/2012 | Miyazaki ............. | F04B 43/082 417/477.3 |
| 8,491,284 B2 * | 7/2013 | Miyazaki .......... | A61M 5/14228 417/474 |
| 8,491,286 B2 * | 7/2013 | Miyazaki ............. | F04B 43/123 417/474 |
| 8,864,474 B2 | 10/2014 | Nelson | |
| 8,920,144 B2 | 12/2014 | Rotem | |
| 8,936,447 B2 | 1/2015 | Abal | |

(Continued)

*Primary Examiner* — Nathan C Zollinger

(57) ABSTRACT

An infusion pump, driven by a camshaft with one or two cams, controls two sets of angularly aligned fingers phased within a sleeve, compressing two parallel flexible tube-sections, drawing fluid from a fluid source, yielding a combined continuous flow of fluid output from the two tube-sections as a function of the camshaft rotation.

9 Claims, 26 Drawing Sheets

(56) References Cited

U.S. PATENT DOCUMENTS

| | | |
|---|---|---|
| 8,944,780 B2 | 2/2015 | Reilly |
| 9,056,160 B2 | 6/2015 | Rotem |
| 9,107,986 B2 | 8/2015 | Bonnette |
| 9,416,775 B2 | 8/2016 | Focht |
| 9,523,359 B1 | 12/2016 | Geschwender |
| 9,795,737 B2 | 10/2017 | Finan |
| 10,004,846 B2 | 1/2018 | Bonnette |
| 10,113,543 B2 | 10/2018 | Rotem |
| 10,808,689 B2* | 10/2020 | Azapagic ................. F04B 9/042 |
| 2007/0154336 A1* | 7/2007 | Miyazaki .......... A61M 5/14228 |
| | | 417/474 |
| 2010/0143168 A1* | 6/2010 | Miyazaki .............. F04B 43/082 |
| | | 417/412 |
| 2011/0028937 A1 | 2/2011 | Powers |
| 2011/0186143 A1* | 8/2011 | Miyazaki .............. F04B 43/082 |
| | | 137/67 |
| 2014/0363313 A1 | 12/2014 | Morris |
| 2017/0218945 A1 | 8/2017 | Rotem |
| 2020/0191134 A1* | 6/2020 | Azapagic .......... A61M 5/14232 |

\* cited by examiner

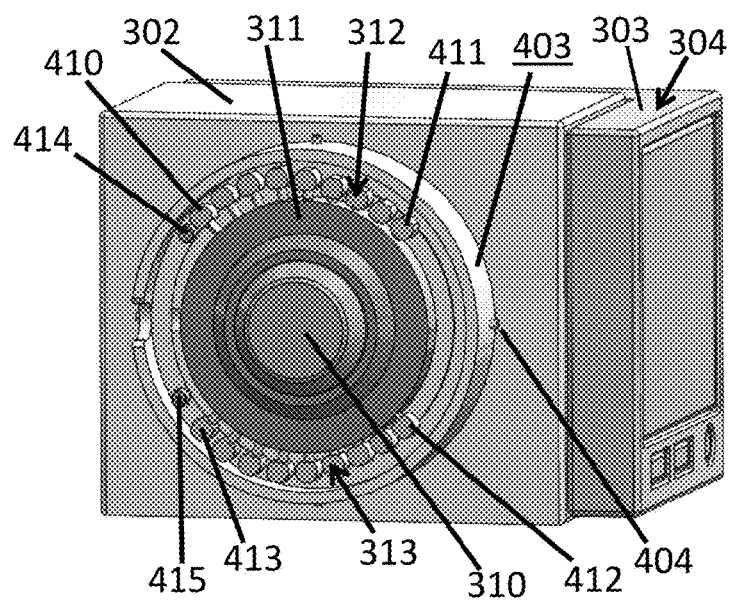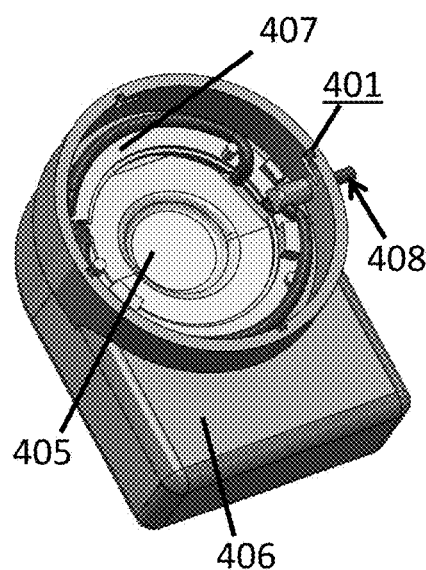
Fig. 4A
Fig. 4B
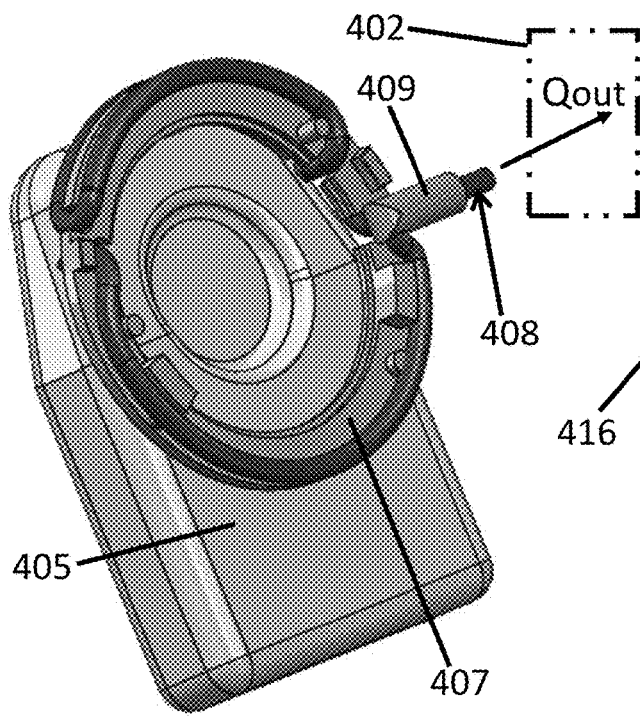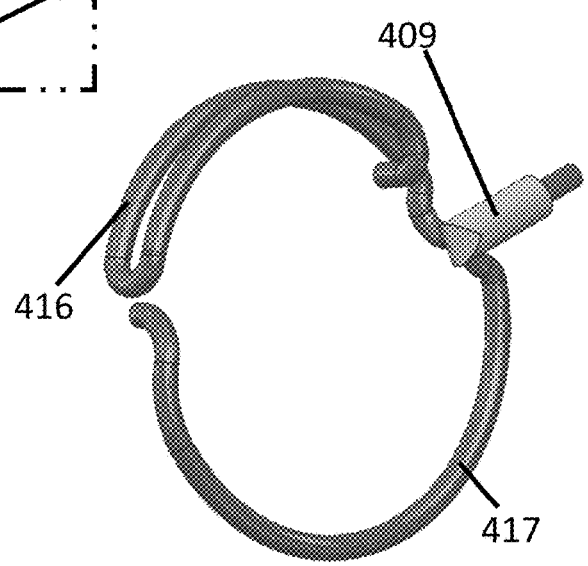
Fig. 4C
Fig. 4D

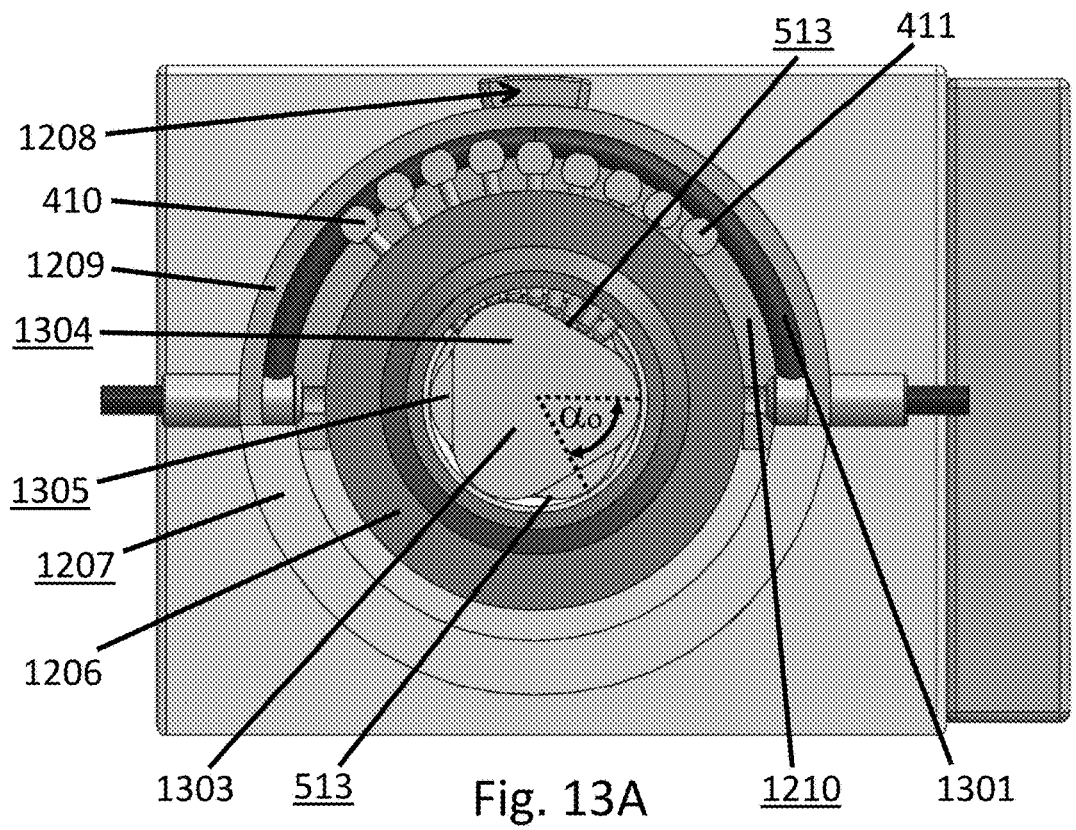
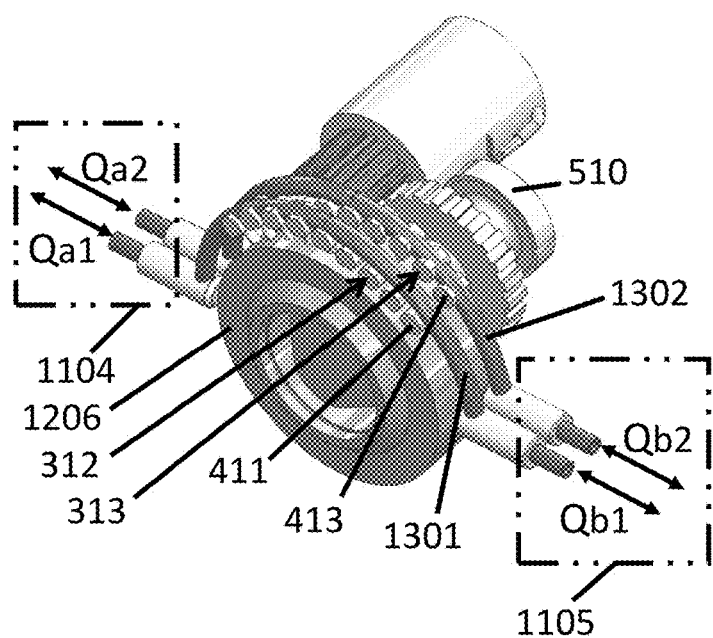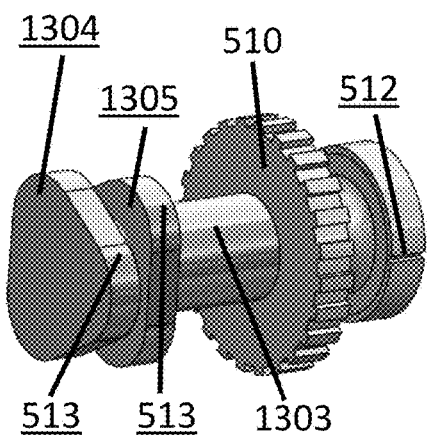
Fig. 13A
Fig. 13B
Fig. 13C

CONTINUOUS FLOW INFUSION PUMP UTILIZING ANGULAR ALIGNED FINGERS

TECHNICAL FIELD

An infusion pump for the medical field, in particular, peristaltic pumps.

BACKGROUND

Medical infusion pumps directly control medical fluid from a source such as an infusion bag or a fluid chamber to a patient. There are many forms of infusion pumps. These include peristaltic pumps as well as piston-driven pumps and multiple pump configurations. The output of a pump delivers fluid flow to the patient with tubing and the relevant components of injecting it to a patient. Piston and peristaltic pumps utilize a linear or rotary movement of parts to control fluid flow to a patient. A syringe pump uses a piston to create the fluid flow to a patient, whereas a peristaltic pump pinches a tube along its length in a controlled manner to provide flow to a patient. Peristaltic type pumps often employ fingers or rollers to pinch and squeeze the tubing to move the fluid through the tube. A list of prior art patents, including the different pump types, is included.

Peristaltic pumps have an inherent operational region where there is no output flow. This no-flow range can approach half of the flow range. These pumps are typically utilized in medical applications to deliver medical fluid from a source such as an infusion bag wherein multiple fingers cyclically pinch the flexible tubing to provide the fluid to a patient. Pump manufacturers typically program the electronics and controller to go quickly through this no-flow region, creating potential problems for the patient.

Two versions of peristaltic pumps will describe how they operate. These prior art pumps typically utilize components and control logic for rotating, sensing, and controlling the camshaft of a pump. FIG. 1A Prior Art is a perspective view of a typical linear peristaltic pump that controls fluid flow through tubing-1 102. The camset-1 101 has a central shaft with multiple cylindrical cams and equal radial offsets from the central axis. This configuration shows nine fingers linearly arranged parallel to the central shaft of camset-101. The corresponding cam of camset-1 101 drives each finger. This style of a peristaltic pump typically has between 4 to 12 fingers. Each cam is offset rotationally from its adjacent cam. A rotary input rotates the camset-1 101 on its central shaft.

The pump's end view, shown in FIG. 1B PRIOR ART, indicates the compression of tubing-1 102 onto tube-stop-1 105. Pump-frame-1 106 maintains camset-1 101 on its central axis. FIG. 1C Prior Art is the front view with the fingers compressing the tubing-1 102. The fingers align with the cams of camset-1 101. An infusion bag (not shown) provides the fluid source for the right end of tubing-1 102. The fluid flow exits the left end of tubing-1 102, providing fluid flow to the patient. The eccentric offset of each cam yields the amount of allowable movement of the fingers against the tubing-1 102. The dashed lines of the tubing-1 102 indicate the surface area of the inner diameter. The action of the fingers distorts the thickness of the tubing, reducing the flow through the tubing. The complexity of portraying the compression of the tubing-1 102 is not displayed.

The compression created with the position of finger-upstream 103 results in the deformation of the upper tube thickness to squeeze into the same thickness as the lower tube thickness, shutting off fluid downstream. Finger-downstream 104 also shuts off the fluid flow to the patent. Finger-upstream 103 and finger-downstream 104 pinch off the tubing-1 102, whereas the central fingers allow fluid to be contained within the tubing-1 102. As camset-1 101 rotates, finger-downstream 104 releases from the tubing-1 102, allowing the fluid within tubing-1 102 to open.

The fingers progressively pinch tubing-1 102 so that the interactions pinch fluid out tubing-1 102 to the patient continuously. When the rotation of camset-1 101 is at its half revolution, the central fingers pinch off the tubing while the right and left ends of tubing-1 102 are open, allowing the output flow to continue. Further rotation of the camset-1 101 results in finger-downstream 104 shutting off flow output from tubing-1 102, as shown in FIG. 1C Prior Art. Although the flow is continuous for more than half of one revolution of camset-1 101, there is no flow output for the remainder of one revolution of camset-1 101. This no-flow portion of the camset-1 101 rotation is the pump's dead-band, typically referred to as the anomalous region of a peristaltic pump.

The camset-1 101 is typically rotated rapidly throughout this anomalous region of no-flow output to shorten the actual timeframe of no-flow output. Flow irregularities can occur during this quick transition once finger-downstream 104 opens. The fluid entrapped within the tubing-1 102 can yield higher internal fluid pressures when the rate of camset-1 101 rotation increases rapidly, leading to a potential undesirable flow surge once the downstream fingers decelerate and then open the tubing-1 102 restrictions. One revolution of the camset-1 101 represents one cycle of the pump. Peristaltic pumps typically have one or two sensors to detect the rotation, one of which monitors when a given cycle occurs. The sensor communicates with the control logic of the pump to maintain the desired rotation. It takes time to respond to a load disturbance even with two sensors, including time to complete a cycle. A disturbance, potentially not detected until a cycle completes, such as upstream or downstream tubing or motor aberrations, can result in un-intended flow in the anomalous region or no flow in the flow region, creating a problem for the patient.

FIG. 2A PRIOR ART portrays a peristaltic pump with finger-in 202, finger-main 203, finger-out 204, and a camset-2 201 with three cams on a single camshaft. Each cam has its unique shape to properly control fluid flow through tubing-2 205. An infusion bag at the right end of tubing-2 205 provides fluid flow, exiting the tubing-2 205 to the patient. FIG. 2B PRIOR ART shows the camset-2 201 pushing finger-in 202 such that the thickness of the one-side-wall of the tubing-2 205 is compressed within the opposite side-wall shutting off input fluid. Tube-stop-2 206 is the seat for tubing-2 205. Pump-frame-2 207 contains camset-2 201 on its central axis and is attached to the tube-stop-2 206. Finger-main 203 is just reaching its most extended position from the centerline of camset-2 201. Finger-out 204 is in its open position, allowing flow from the action of finger-main 203 to go out the tubing-2 205 to the patient.

As camset-2 201 rotates, finger-out 204 shuts off, finger-in 202 opens, and finger-main 203 opens the tubing-2 205 to suction the flow from the source. Further rotation of camset-2 201 pinches off tubing-2 205 at finger-in 202. At this camset-2 201 position, finger-in 202 and finger-out 204 pinches off the flow, finger-main 203 compresses the internal volume of the tubing to set up a flow surge out the region of finger-out 204 once the finger-out 204 retracts and allows the output surge of flow. The shape of each of the three cams of camset-2 201 yields output flow in pulses with finger-main 203 generating flow pulses timed by its interaction with both finger-in 202 and finger-out 204. Depending on their profile, the cams deliver one or two pulses of output flow per revolution of camset-2 201. Similar to FIG. 1A PRIOR ART, a disturbance can result from the un-intended flow or un-intended no-flow, creating a problem for the patient.

These prior art peristaltic pumps can also be configured (not shown) with the fingers or rollers radially oriented to the central axis of the camshaft utilized. These prior arts do not yield continuous flow output through the tubing. Several loading conditions or camshaft rotation intermittent problems can occur during the transitions between flow and no-flow, resulting in unsafe fluid delivery to a patient.

SUMMARY

Twelve embodiments will be shown and described, each providing a continuous fluid flow as a function of the camshaft rotation. These embodiments utilize a camshaft to control two sets of fingers to control the fluid flow through two tube sections. The fingers are arranged angularly on the same axis as the camshaft. These two tube sections have an inlet and an outlet wherein the combined output is a continuous fluid flow. Five of the twelve embodiments share the same method of installing and removing the cassette and tubing assemblies. The other seven embodiments employ different means of assembling and removing cassette and tubing assemblies. The reference numbers underlined in the drawings and descriptions emphasize and distinguish them from the actual parts. Subassemblies and complete assemblies utilize an arrow on their lead lines. The conclusion will also summarize how all of the embodiments yield continuous flow. In addition, the conclusion will summarize the technical terms used throughout the embodiments.

BRIEF DESCRIPTION OF THE DRAWINGS

Twelve embodiments of continuous flow pumps will be described. These embodiments utilize a rotational arrangement of two sets of fingers controlling two tube sections. FIG. 3A Embodiment-A through FIG. 6D shows the components of Embodiment-A.

Two methods of interchanging the cassettes and tubing from the pump assembly, based on the embodiment, are shown.

Most infusion pumps employ upstream and downstream sensors to detect source fluid potential problems such as occlusions to the fluid continuity and monitoring for air entrapments which can be detrimental to the patient. These sensors monitor the tubing to monitor potential problems. Other locations and quantities of upstream and downstream sensors are possible. These sensors, electronics, hardware, and control-logic software are well understood in infusion pumps and are not the focus of the embodiments discussed.

DETAILED DESCRIPTION

Figure 1A:
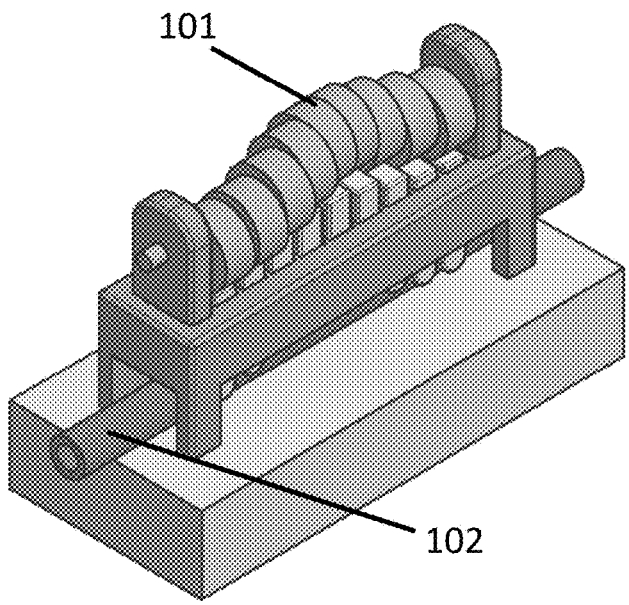
FIG. 1A PRIOR ART, FIG. 1B PRIOR ART, and FIG. 1C PRIOR ART show a pump with a linear arrangement of components.
Figure 1B:
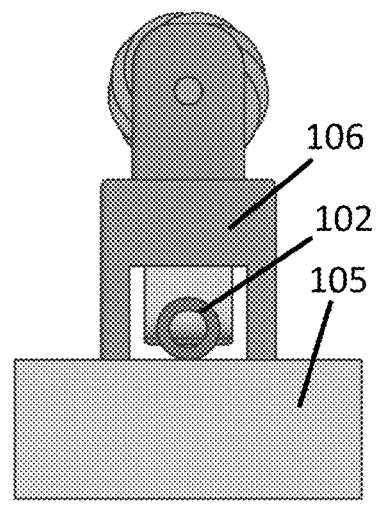
Figure 1C:
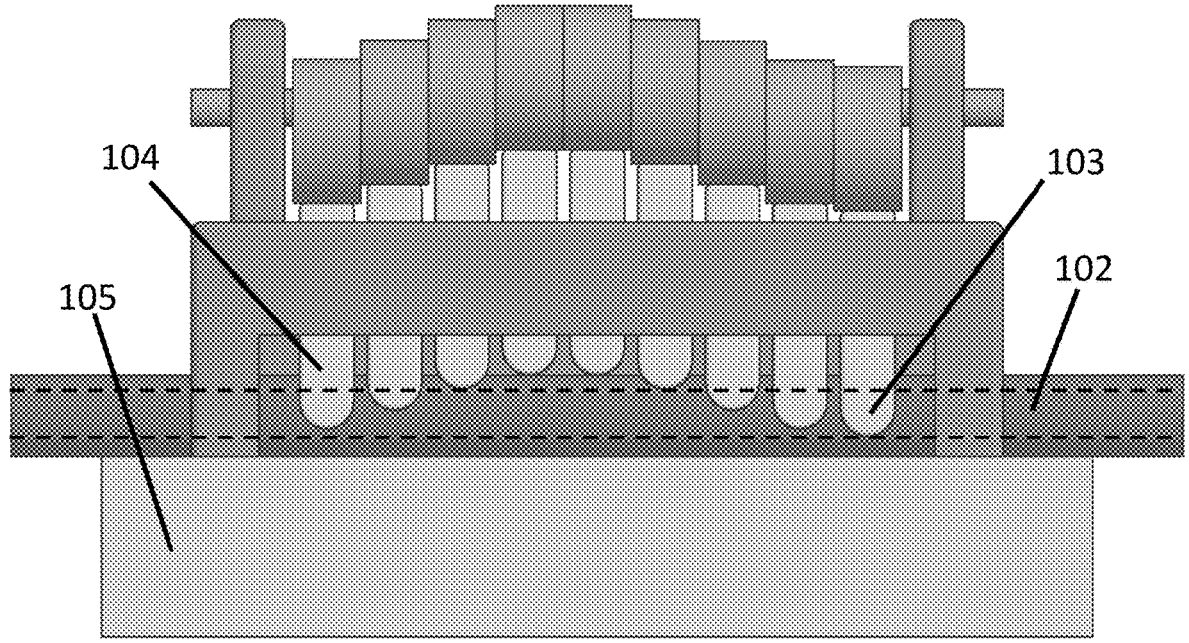
Figure 2A:
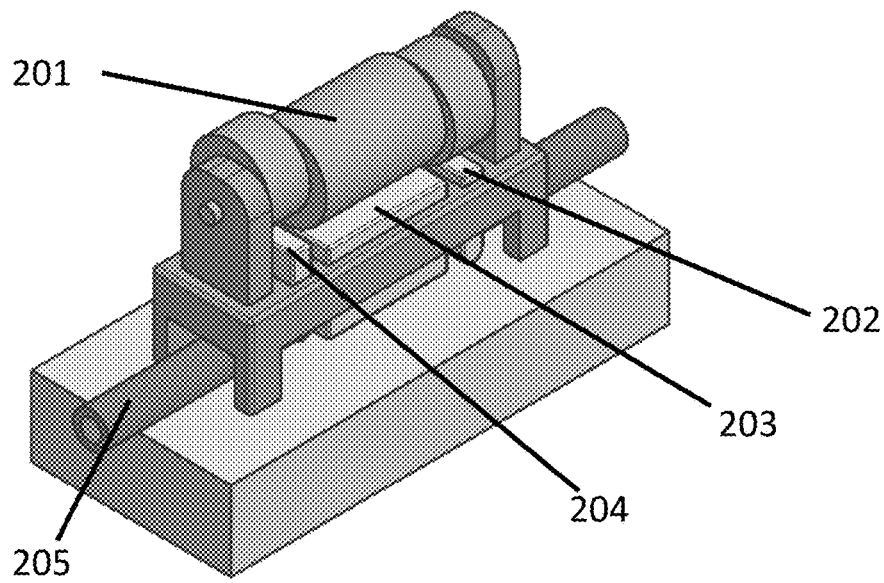
FIG. 2A PRIOR ART and FIG. 2B PRIOR ART show a rotary arrangement of components.
Figure 2B:
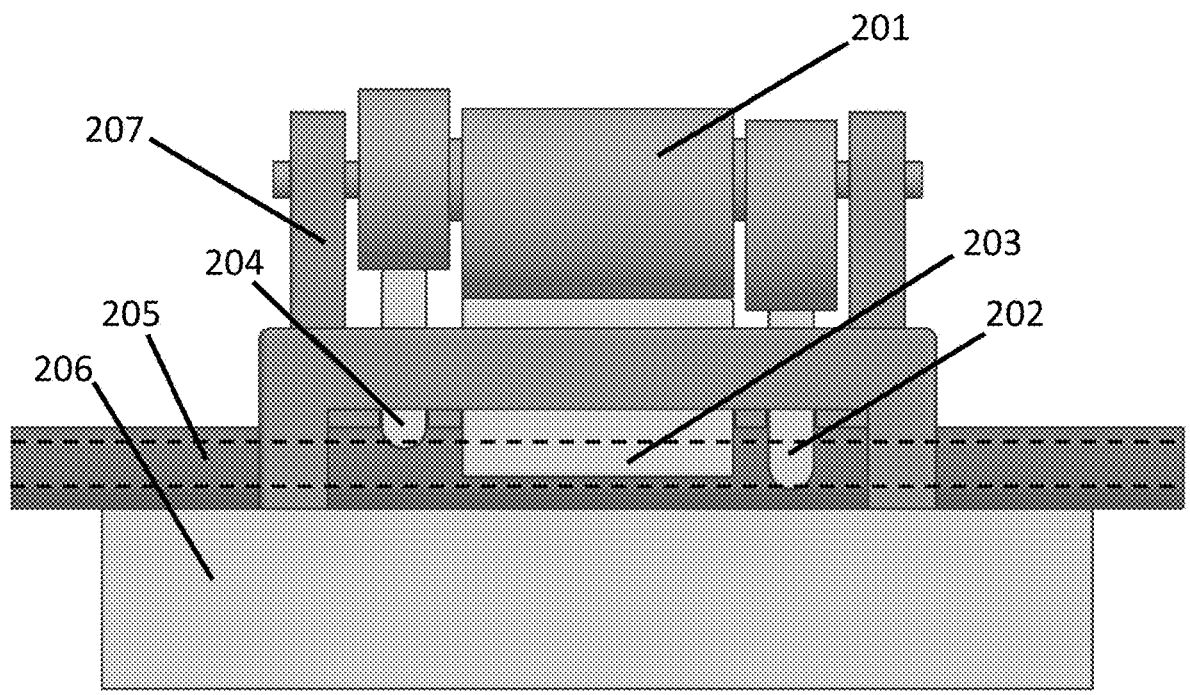
Figure 3A:
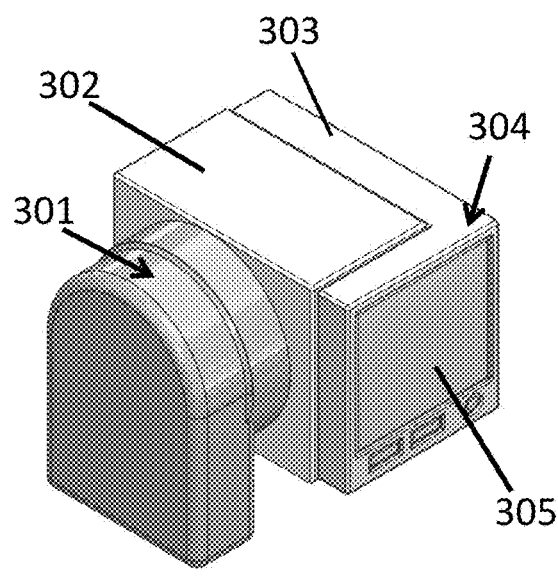
FIG. 3A Embodiment-A, FIG. 7A Embodiment-B, FIG. 14B Embodiment-F3, FIG. 15D Embodiment-G3, and FIG. 16 Embodiment-G4 utilize an internal infusion bag, typically used in ambulatory or other non-stationary applications. The other seven embodiments utilize a remote fluid source. The internal infusion bag would typically be utilized for an ambulance and personal use, whereas stationary applications typically utilize an external infusion bag. Non-medical and some medical applications utilize FIG. 11A Embodiment-E, FIG. 12A Embodiment-F1, and FIG. 15A Embodiment-G1, providing two-way fluid flow.

FIG. 3A Embodiment-A is one of twelve embodiments yielding continuous flow output. All twelve embodiments have batteries that allow the pump configurations to have both DC and AC input power options. An ambulatory, mobile version would have batteries, whereas a hospital version would typically utilize AC power. This embodiment consists of two subassemblies, cassette-assembly-A 301 and pump-assembly-1 304. The cassette-assembly-A 301 is attached to base-1 302 attached to housing 303. Screen 305 provides an interface for the user. Other interface components, including a USB port (not shown), are options for a given embodiment. The front view of the pump is at the same viewing angle as the screen 305. All of the embodiments perform the same function of yielding continuous-flow output as a function of the camshaft rotation.

Figure 3B:
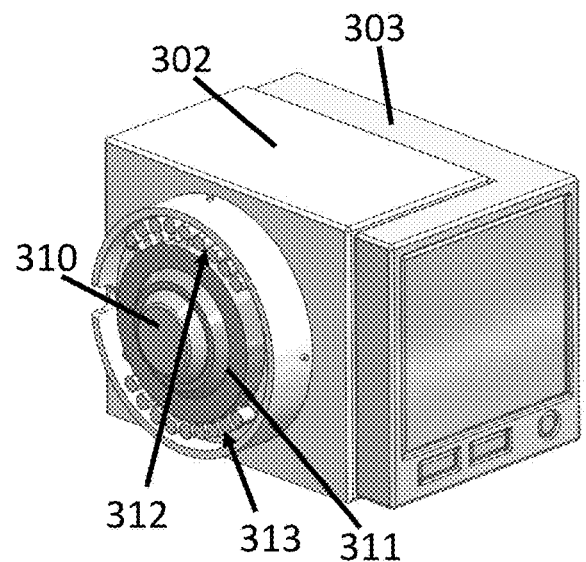
Figure 3C:
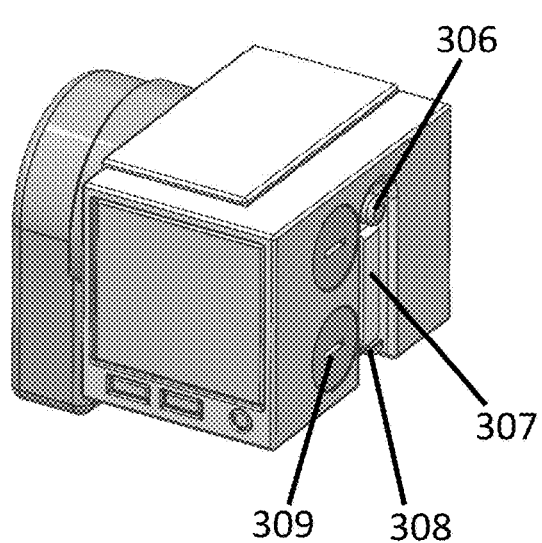
Figure 3D:
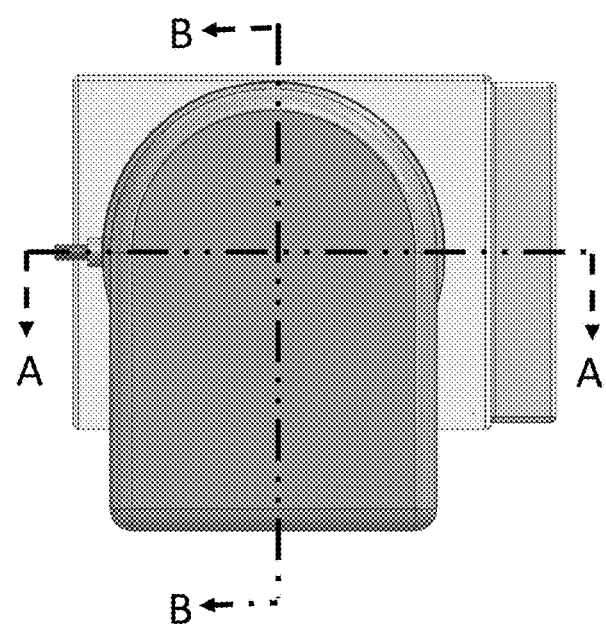

FIG. 3B is a perspective of the pump-assembly-1 304. Cover 310 seals the pump-assembly-1 304 from its internal parts. Finger-set-1 312 and finger-set-2 313 are contained within the sleeve-1 311. FIG. 3C is a perspective view including lever-guide 306, lever 307, lever-assist 308, and battery-access 309. Two battery-access 309 plugs allow the replacement of the batteries. The battery size and quantity are a function of the power range of the pump. This embodiment utilizes two size-D batteries. Other embodiments not discussed would use less power, utilizing smaller batteries yielding a smaller pump. FIG. 3D is the left-end view that defines section A-A described in FIG. 5A and section B-B described in FIG. 6A.

FIG. 4A is a perspective view of the pump-assembly-1 304 of FIG. 3A Embodiment-A. FIG. 4B is a perspective view of this embodiment's cassette-assembly-A 301. Sleeve-1311 maintains multiple fingers in their proper orientation. Sleeve-1311 has holes that provide the sliding surfaces for each finger. The holes can be cylindrical or slot-shaped to house the finger style employed for all embodiments. For example, finger-1a 410 and finger-9a 411 are two of the fingers of finger-set-1 312, whereas finger-1b 412 and finger-9b 413 are two of finger-set-2 313. The annular-flange-1 403 of base-1 302 provides mating with the cassette-assembly-A 301, and it retains the tubing-assembly-1408 shown in FIG. 4B, FIG. 4C, and FIG. 4D. The inner surface of the annular-flange-1403 is the tube-seat retaining the compression of tubing-assembly-1 408 as finger-set-1 312 and finger-set-2 313 traverses in sleeve-1 311. Tube-seat describes a surface utilized for various parts to retain the tubing of a given embodiment. Sensor-upstream 414 monitors the upstream fluid of tubing-assembly-1 408, whereas sensor-downstream 415 monitors the downstream fluid of tubing-assembly-1408.

Cassette-A 406 has multiple locking-recess 401 features. A component feature has its reference number underlined to distinguish the feature from the part or assembly. Similarly, an arrow on a lead line represents each sub-assembly or main assembly. Mounting the cassette-assembly-A 301 unto the annular-flange-1403 of base-1302 is accomplished with the pin-cassette 404 mated with locking-recess 401 of cassette-A 406. The cassette-assembly-A 301 is twisted clockwise onto the annular-flange-1 403 to lock the cassette-A 406 and cassette-assembly-A 301 into place. Other methods (not shown) of locking the cassette-A 406 onto base-1302 include snap-fits, latches, and a variety of fasteners. Tube-hold-1407 guides the assembly of tubing-assembly-1408 and the infusion-bag-internal 405.

FIG. 4C is the cassette-assembly-A 301 without the cassette-A 406 to portray the tubing-assembly-1408 attached to the infusion-bag-internal 405. Tube-hold-1407 provides an assembly guide for placing the tubing-assembly-1408 into the cassette-assembly-A 301. FIG. 4D is the tubing-assembly-1 408. Tube-section-1 416 is the tubing that interfaces with finger-set-1 312, whereas tube-section-2 417 is the tubing that interfaces with finger-set-2 313. Connector-output 409 combines the two tube sections to provide continuous flow output Qout to the infusion-patient 402. The infusion-patient 402 includes peripherals between the connector-output 409 and the actual patient, including filters, a variety of catheters, and other administrative components to provide the medical fluid to the patient. Cassette-A 406 could include features to remove the need for tube-hold-1407.

The output flow Qout of all embodiments depends on the tubing size and structure, the camshaft rotary displacement and velocity, the number of fingers compressing the tubing, and the upstream fluid pressures downstream of the pumping environment. Increasing the input rotary camshaft velocity will increase the flow-rate output Qout and volume output Vout. Flow output Qout of an infusion pump is typically rated and defined as milliliters per minute or hour, wherein the fluid volume Vout is in milliliters. Tube-section-1416 and tube-section-2 417 have physical properties ideal for medical infusion, including elasticity and resiliency, wherein the tubing springs back into shape when not compressed.

Figure 5A:
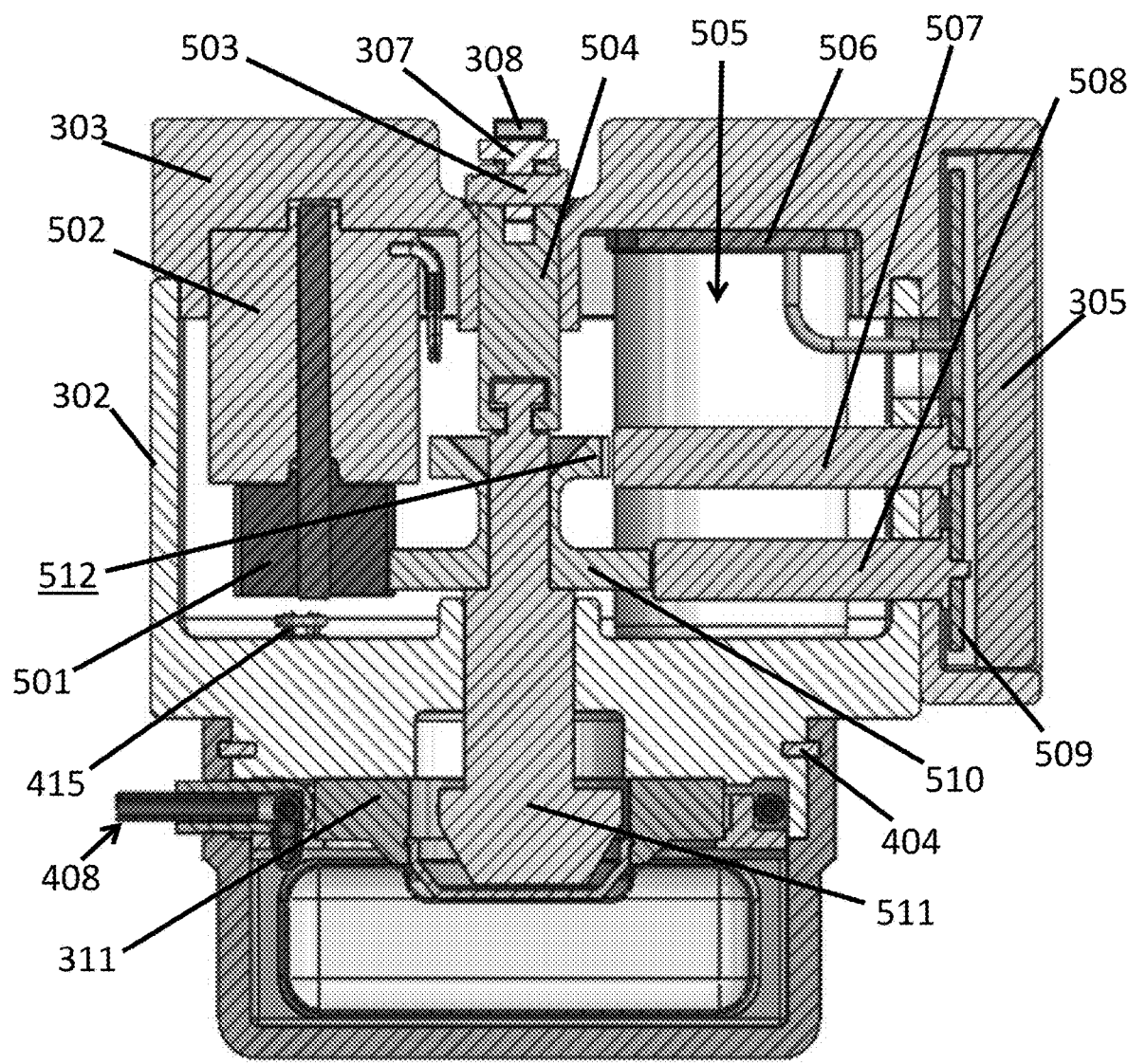

FIG. 5A is sectional-view A-A showing the top of the infusion pump as described in FIG. 3D. Motor 502 drives gear-motor 501 to drive gear-camshaft 510 attached with camshaft-1 511. Camshaft-1 511 interacts with other components shown in FIG. 6A. Camshaft-1 511 is guided with camshaft-assist 504 and rotates in the central hole of base-1 302. Pin-pivot 503 connects camshaft-assist 504 with lever 307. Housing 303 envelops the battery-assembly 505 and the battery-board 506. Cycle-indicator 512 of gear-camshaft 510 aligns with sensor-cycle 507. Sensor-cycle 507 monitors the rotation of the gear-camshaft 510 and therefore camshaft-1 511 at 120-degree increments of gear-camshaft 510 rotation yielding one cycle of 120-degrees. Sensor-camshaft 508 monitors the gear pulses, and the combination of sensors works together. Board-main 509 is the electrical board with the control logic and interconnections with the electrical components and the screen 305.

A mobile application, known as a mobile app, shown in FIG. 16A Embodiment-G4, replaces screen 305, including shared control logic software. The control logic typically utilizes an input signal to drive the embodiment as a voltage or current, dependent upon the circuitry involved. The embodiment's continuous fluid flow output is a function of the input signal, and the flow output is proportional to the electrical signal. Although the function of the embodiments is to control the input signal, current, or voltage, to yield continuous flow output, the emphasis of all of the embodiments is the camshaft rotary position and its rotary velocity. The function of the motor 502 and the gearing to the camshaft 511 is to provide an angular rotation proportional to its input signal.

Figure 5B:
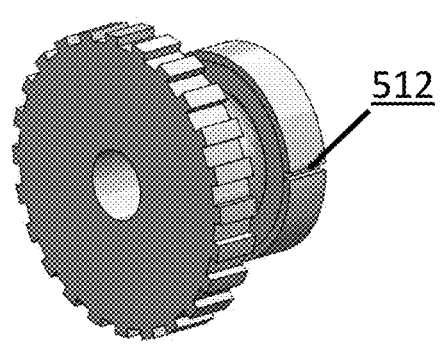
Figure 5C:
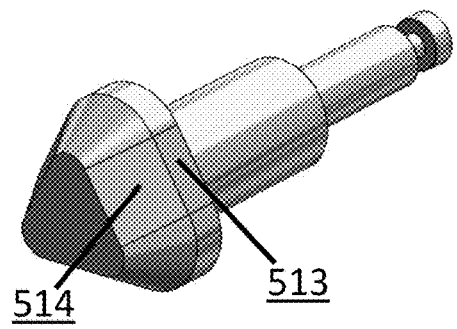

FIG. 5B is gear-camshaft 510 with the recessed slot of cycle-indicator 512. FIG. 5C shows the perspective view of the camshaft-1511. The cam-profile 513 is the surface of the cam generated as an equilateral triangle, spanning the width shown wherein the corner radii are equal. This cam-profile 513 is the surface that yields linear longitudinal translation within sleeve-1311 of the finger-set-1312 and finger-set-2 313 as described in FIG. 19B cycle-home through FIG. 24B. Two-dimensional geometry cam-profile 513 and its surface, also called cam-profile, are utilized interchangeably for all embodiments. This cam-profile 513 also sets the range of movement of finger-set-1 312 and finger-set-2 313 within the sleeve-1311. The range of any given finger longitudinal translation is established in the geometry of the cam-profile 513 as the camshaft-1 511 rotates. A cycle is one-third of the camshaft-1 511 rotation equating to 120-degrees. Cam-taper 514 is the radial-tapered blend from the cam-profile 513 inward toward the central axis up to the end of the camshaft-1-511. Cassette-assembly-A 301 cannot be removed or installed until camshaft-511 moves axially to employ the cam-taper 514. The cam-taper 514 surface blends from the cam-profile 513 surface, tapering to the end of the camshaft. The cam-profile 513 and the cam taper 514 comprise the cam of camshaft 511. FIG. 25A Camshaft-Retraction through FIG. 26C describes this camshaft-1511 as it retracts, during which the fingers switch from contacting the cam-profile 513 surface to the surface of the cam-taper 514.

Figure 6A:
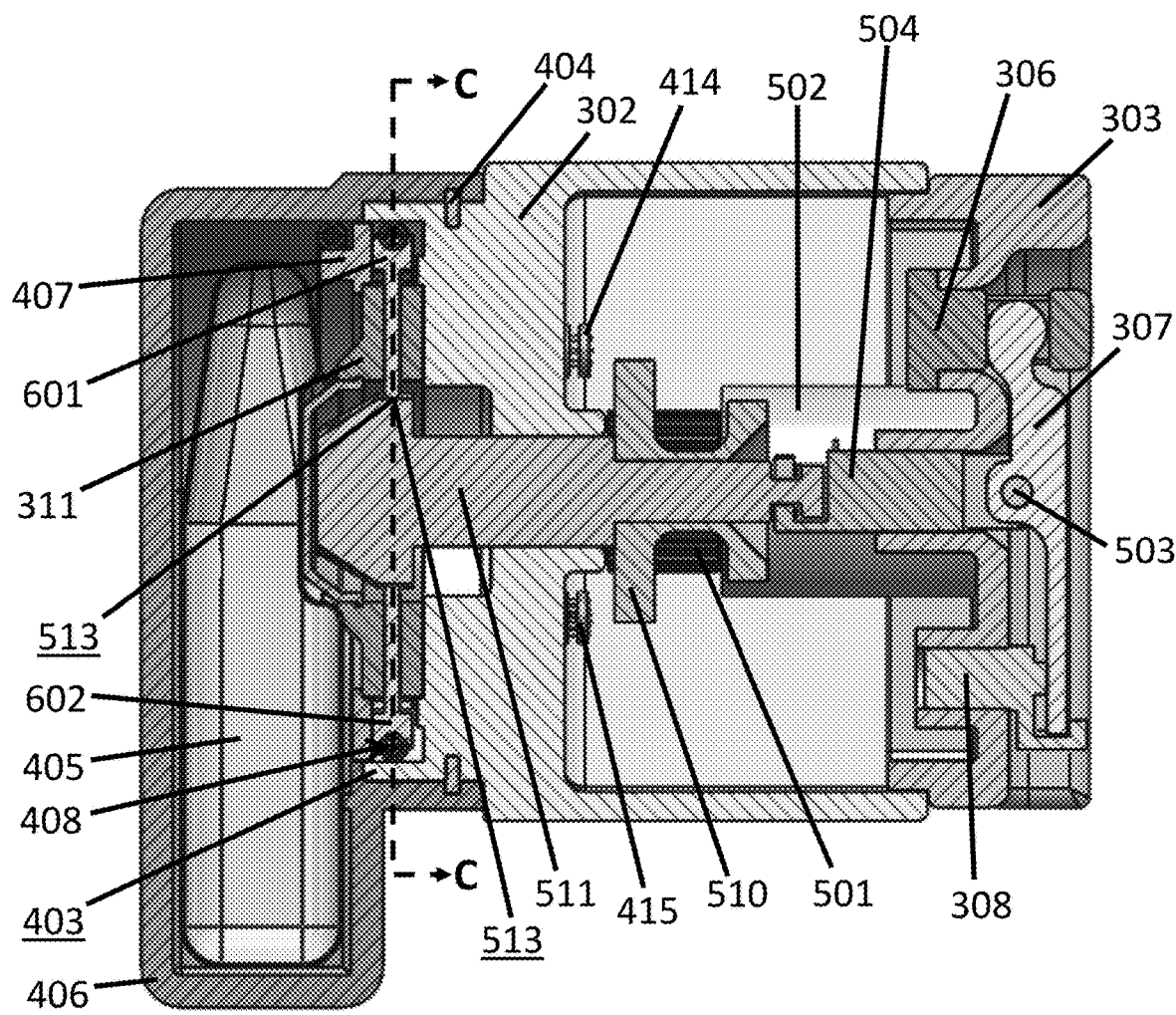

FIG. 6A is sectional view B-B as described in FIG. 3D. Section C-C, shown in FIG. 19B cycle-home through FIG. 23B, describes the continuous-flow operation of the embodiments. Camshaft-1511 rotates in the bore in base-1 303 of pump-assembly-1 304 in response to the motor 502 rotation via the gear-motor 501 and gear-camshaft 510. This rotation radially moves finger-5a 601 within one of the holes of sleeve-1 311. Lever 307 and camshaft-assist 504 keep the axial alignment of camshaft-1 511. Tubing-assembly-1 408 is compressed by the finger-5a 601 and finger-5b 602. The annular-flange-1 403 supports the tubing-assembly-1408 from moving radially outward with respect to the axis of camshaft-1 511. The term tube-seat will reference this inner surface of annular-flange-1403. Regarding compression, the inactive tubing region is the tubing-assembly-1408 on the left side of tube-hold-1407. When activated, lever 307 and camshaft-assist 504 allow axial movement of camshaft-1511 to remove cassette-assembly-A 301. FIG. 25A Camshaft- Retraction through FIG. 26C describes the lever 307, lever-guide 306, and lever-assist 308 interactions. Section line C-C serves as the plane of action of camshaft-1 511, wherein the cam-profile 513 is on the same plane as the sleeve-1311 holes for both finger-set-1 312 and finger-set-2 313. The central axis of the holes establishes this plane of action. The continuous-flow operation section of FIG. 19a Camshaft-Rotation through FIG. 24B describes the tubing compression by finger-set-1 312 and finger-set-2 313.

Figure 6B:
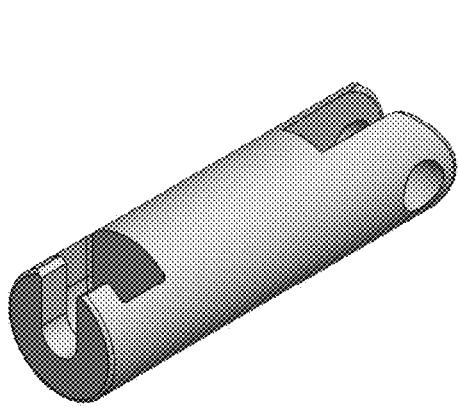
Figure 6C:
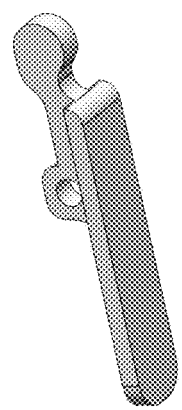
Figure 6D:
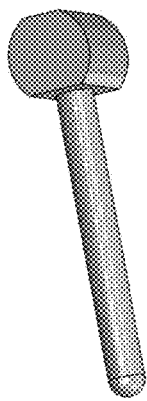

FIG. 6B is the camshaft-assist 504, which shows the clevis-type-joint recess, allowing camshaft-1 511 rotation and retraction. Pin-pivot 503 maintains the axial movement of camshaft-assist 504, providing a pivot for the lever 307 when activated. The camshaft-1511 does not move axially during the pump's operating function of providing continuous flow. FIG. 6C is a perspective view of lever 307. FIG. 6D is finger-5a 601.

Embodiment-B Through Embodiment-D

Figure 7A:
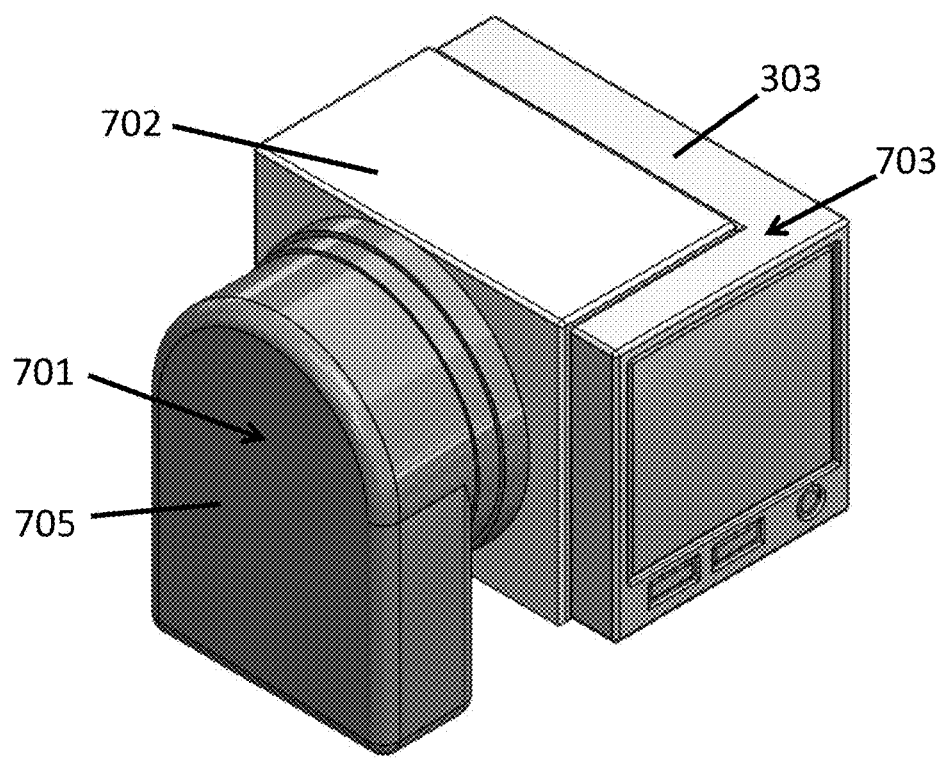
FIG. 7A Embodiment-B through FIG. 7C shows the components of Embodiment-B.
Figure 7B:
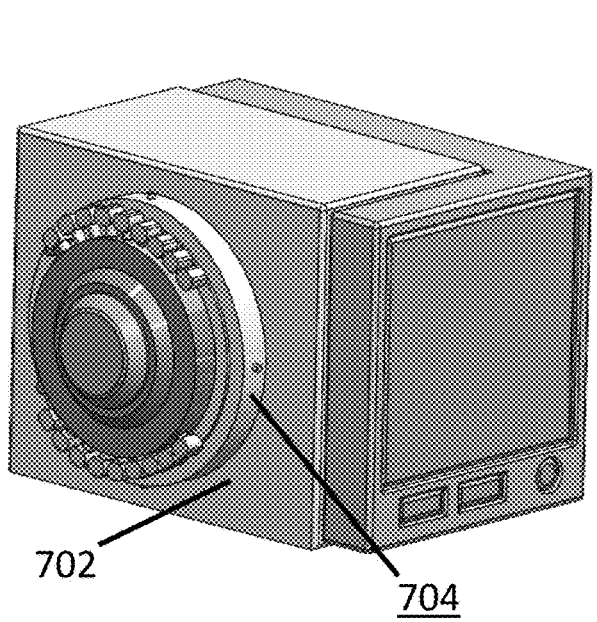
Figure 7C:
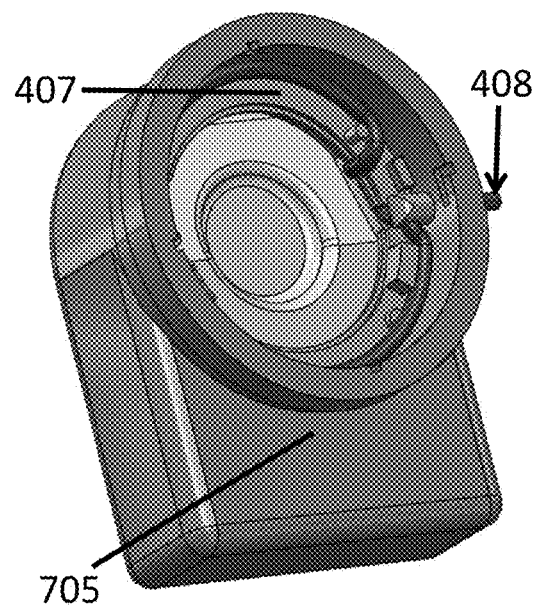

FIG. 7A Embodiment-B, comprised of the assembly pump-assembly-2 703 and cassette-assembly-B 701, is similar to embodiment-A with a different way of containing the tubing-assembly-1 408. FIG. 7B is a perspective view of pump-assembly-2 703. Annular-flange-2 704 of base-2 702 is the mounting feature for the cassette-B 705. FIG. 7C is a perspective view of the cassette-assembly-B 701 containing tubing-assembly-1408. This embodiment utilizes the cassette-B 705 to keep the tubing-assembly-1408 radially in place respective to the axis of the camshaft-1511. The cylindrical internal surface of cassette-B 705 is the tube-seat, performing the same function as the annual-flange-1403 of FIG. 3A Embodiment-A. The tube-hold-1407 will not be required if its function is designed within cassette-B 705 to guide the tubing-assembly-2 803.

Figure 8A:
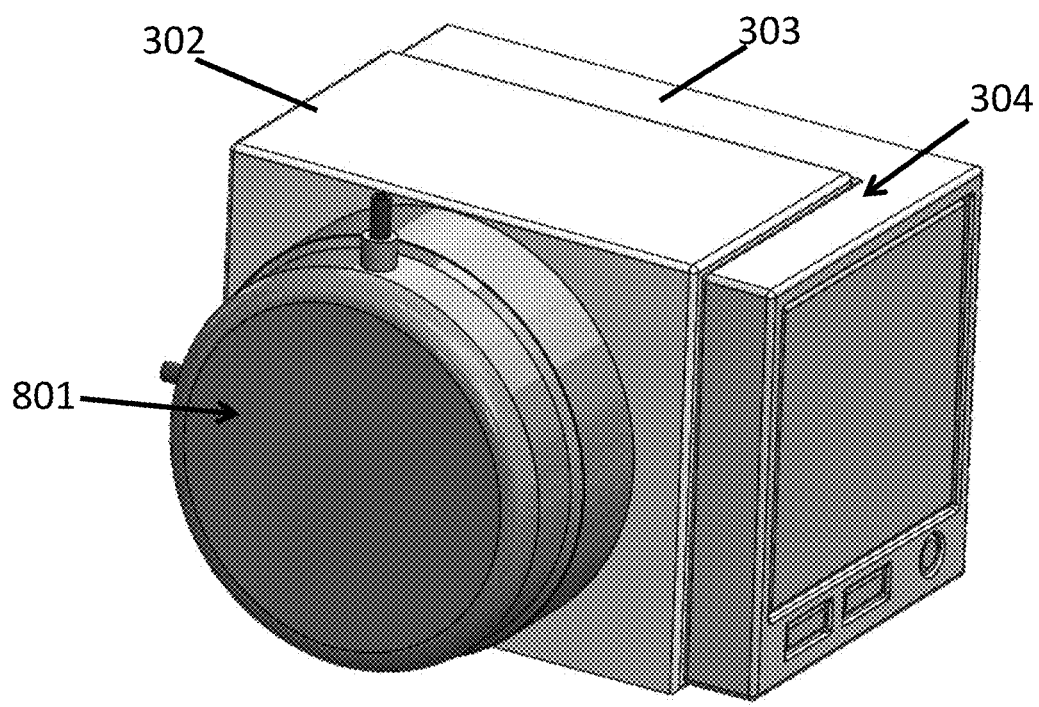
FIG. 8A Embodiment-C and FIG. 8B show the components of Embodiment-C.
Figure 8B:
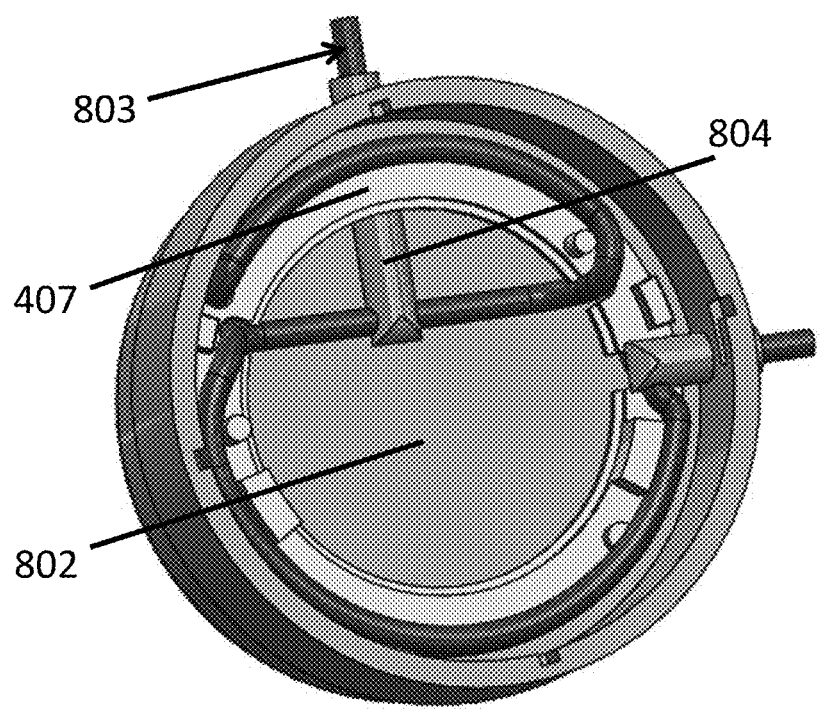

FIG. 8A Embodiment-C consists of cassette-assembly-C 801 and pump-assembly-1 304. FIG. 8B is a perspective-view of cassette-assembly-C 801 containing cassette-C 802, the tube-hold-1407, and the tubing-assembly-2 803. Tubing-assembly-2 803 is the same as tubing-assembly-1408 with extra tubing and the connector-input 804. This embodiment does not contain an infusion bag within the cassette. Cassette-C 802, similar to cassette-A 406, is mated with the annular-flange-1403 of pump-assembly-1 304, wherein the inside diameter surface is the tube-seat. The tube-hold-1407 isn't essential if cassette-C 802 includes features to guide the tubing-assembly-2 803. Manual installation of tubing-assembly-2 803 is an option.

Figure 9A:
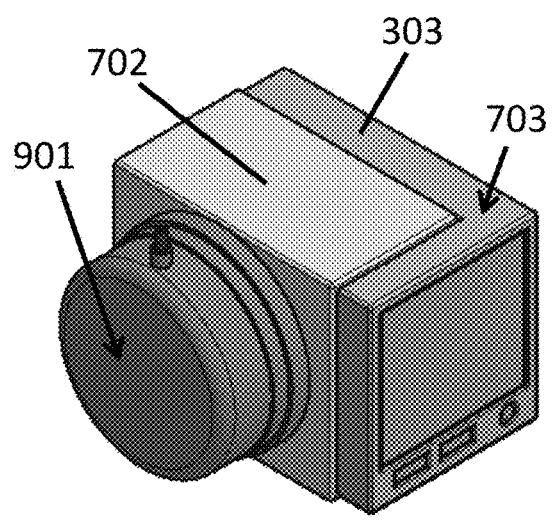
FIG. 9A Embodiment-D through FIG. 9C shows the components of Embodiment-D.
Figure 9B:
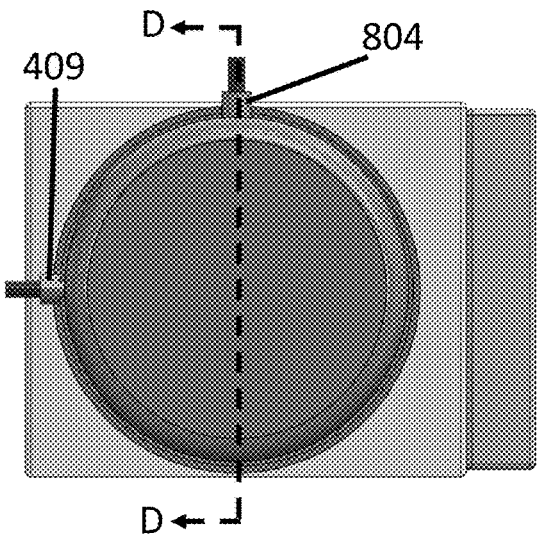
Figure 9C:
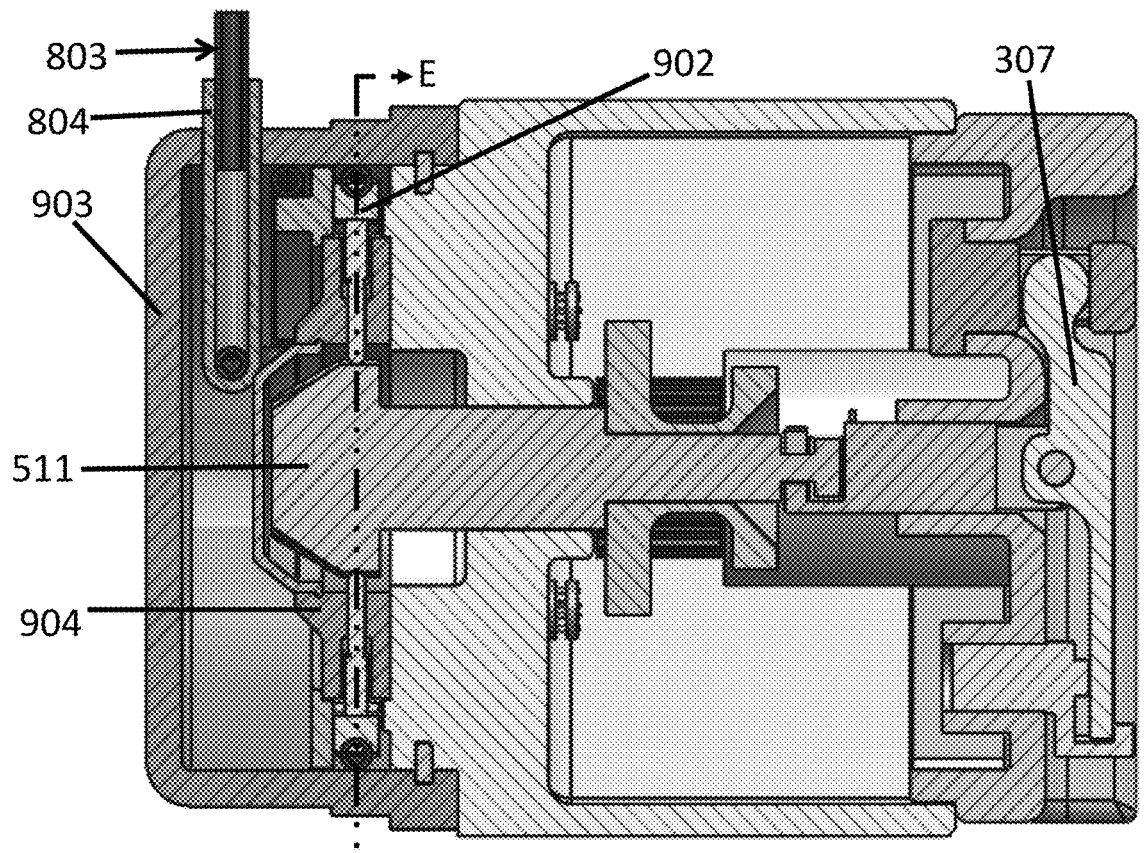
Figure 17A:
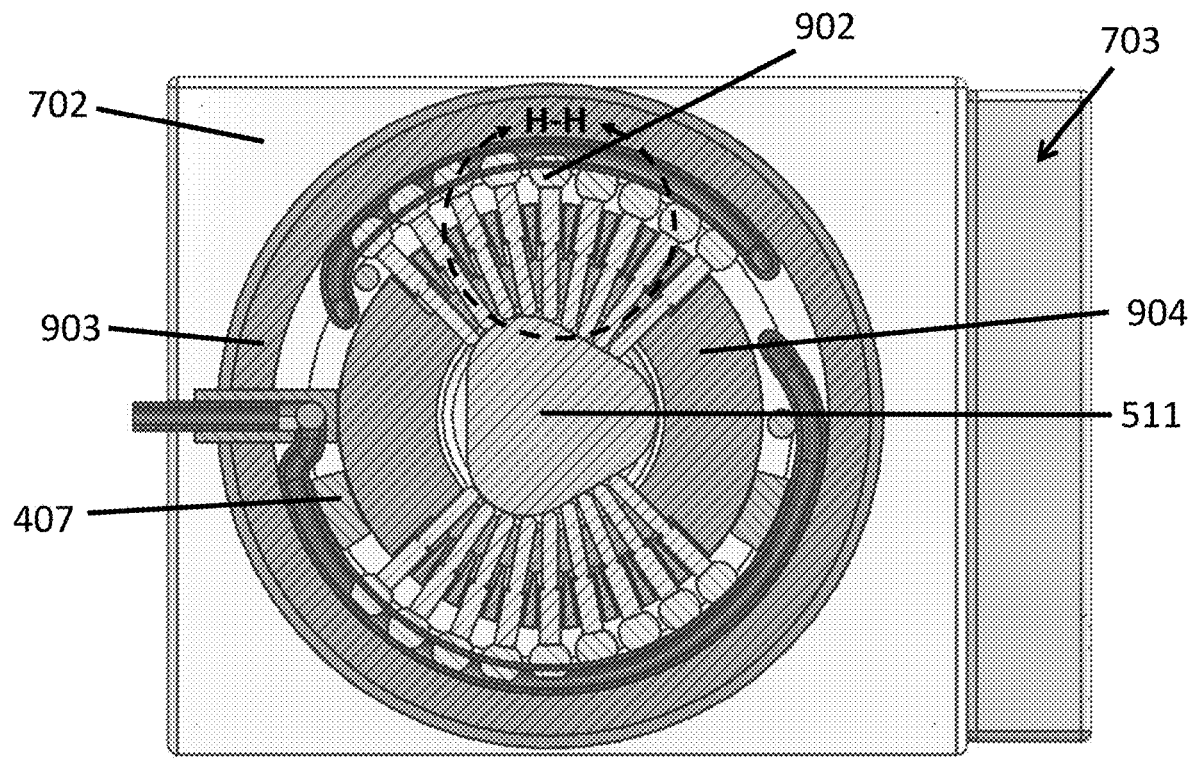
FIG. 17A through FIG. 17C describe containment for the fingers within a sleeve.

FIG. 9A Embodiment-D is a perspective view of another embodiment utilizing a cassette-assembly-D 901 without an internal infusion bag. FIG. 9B is a left-end view of this embodiment, defining section D-D. FIG. 9C is section D-D showing the interior components of this embodiment. This embodiment has two sub-assemblies, cassette-assembly-D 901 and pump-assembly-2 703. There are several notable differences between FIG. 9c and FIG. 6A. The tubing-assembly-1 408 of FIG. 6A is contained radially by the inner diameter of the annular-flange-1403. It is referenced as the tube-seat, whereas tubing-assembly-2 803 of FIG. 9c is held radially by the internal surface of the cylindrical opening of cassette-D 903, which is the tube-seat. Similar to FIG. 7A Embodiment-B, the tube-hold-1 407 isn't needed if cassette-D 903 includes features to guide the tubing-assembly-2 803. FIG. 6A Embodiment-A has an infusion-bag-internal 405, whereas FIG. 9B Embodiment-D has connector-input 804 attached to cassette-D 903. Finger-5c 902 is positioned in sleeve-2 904, providing axial movement created from camshaft-1 511. FIG. 9C defines section E-E, described in FIG. 17A through FIG. 17C and FIG. 25A Camshaft-Retraction through FIG. 26C. The section line E-E also serves as the plane of action of camshaft-1511, wherein the cam-profile 513 is on the same plane as the sleeve-2 904 holes for finger-5c 902 and all of the other fingers as described in FIG. 25A Camshaft-Retraction-full and FIG. 26A Camshaft-Retraction-partial. FIG. 17a section F-F through FIG. 17c describes the functioning of Finger-5c 902.

Tubing Assemblies and their Features

Figure 10A:
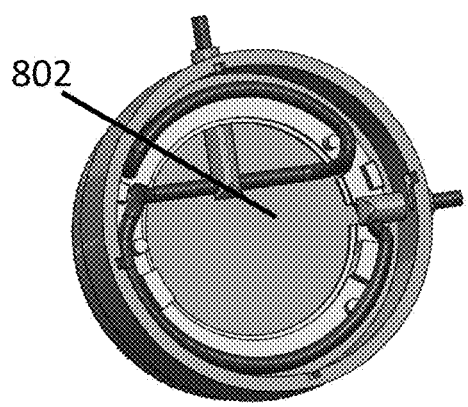
FIG. 10A through FIG. 10D show the tubing assemblies' features describing the tube regions that interface with the fingers and the resulting continuous flow generation.
Figure 10B:
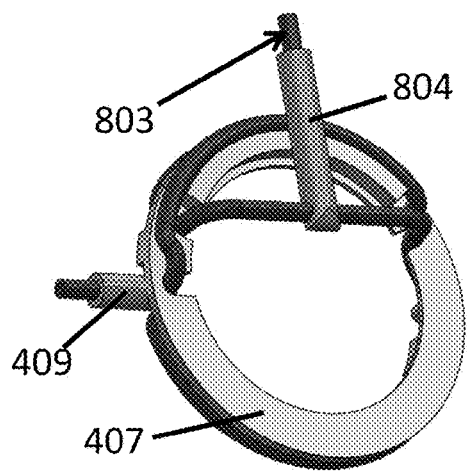
Figure 10C:
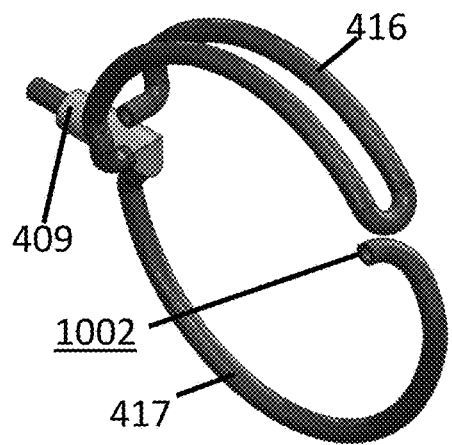
Figure 10D:
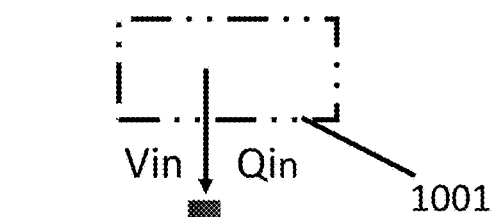
Figure 10D:
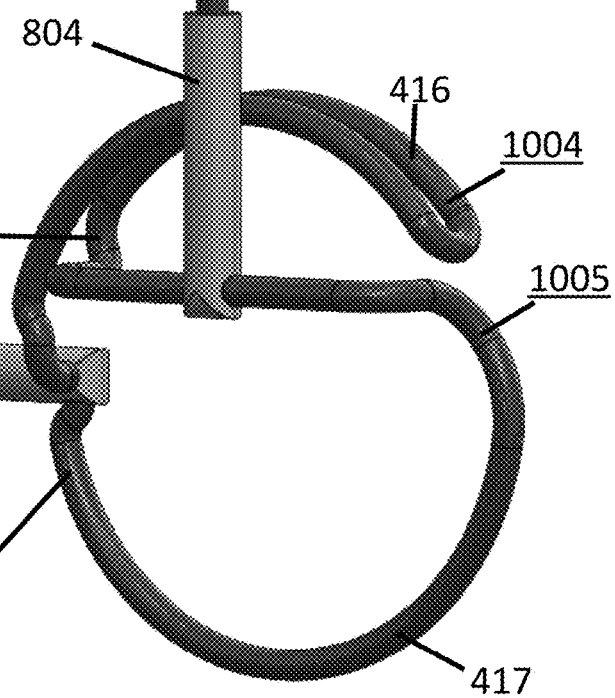

FIG. 10A is a perspective view of cassette-assembly-C 801. FIG. 1013 is another perspective-view of cassette-assembly-C 801 without cassette-C 802. The tubing-assembly-2 803 utilizes the tube-hold-1 407 for assembly. FIG. 10C is tubing-assembly-1 408, including connector-output 409. Cassette-assembly-A 301 and cassette-assembly-B 701 both utilize tubing-assembly-1408. Each tube-end-bag 1002 could be combined to yield a single tube. FIG. 10D is a perspective view of tubing-assembly-2 803, utilizing connector-input 804 and connector-output 409. Connector-input 804 directs the input-flow Qin and the input volume Vin from the infusion-bag-external 1001. Connector-output 409 provides the output-flow Qout and the output volume Vout from the pump to the infusion-patient 402. Infusion-bag-external 1001 includes various items, including administrative sets, check-valves, multiple infusion bags, and other medical components. Tubing-assembly-2 803 is the same as tubing-assembly-1408, with extra tubing added to tube-end-bag 1002 at two locations combined with the connector-input 804. Cassette-assembly-C 801 and cassette-assembly-D 901 both utilize tubing-assembly-2 803. Tubing-assembly-1408 utilizes the inner surface of the annular-flange-1403 of base-1302 for retaining the tubing-assembly-1408 for both cassette-assembly-A 301 and cassette-assembly-C 801. Tube-assembly-2 803 uses cassette-B 705 and cassette-D 903 as the tube-seat.

FIG. 10D also defines four regions of the tubing to describe how the two sets of fingers provide continuous flow-output Qout and volume-output Vout to the infusion-patient 402. Tube-upper-in 1003 represents the input tubing region for the finger-set-1312. Tube-upper-out 1004 represents the output tubing region for the finger-set-1312. Tube-lower-in 1005 represents the input tubing region for the finger-set-2 313. Tube-lower-out 1006 represents the output tubing region of the finger-set-2 313. The flow of fluid is clockwise from tube-upper-in 1003 to tube-upper-out 1004. Similarly, fluid flow is clockwise from tube-lower-in 1005 to tube-lower-out 1006. The output flows from the tube-upper-out 1004 and the tube-lower-out 1006 combine at the connector-output 409 to yield the output fluid flow Qout and output volume Vout to the infusion-patient 402.

Figure 19A:
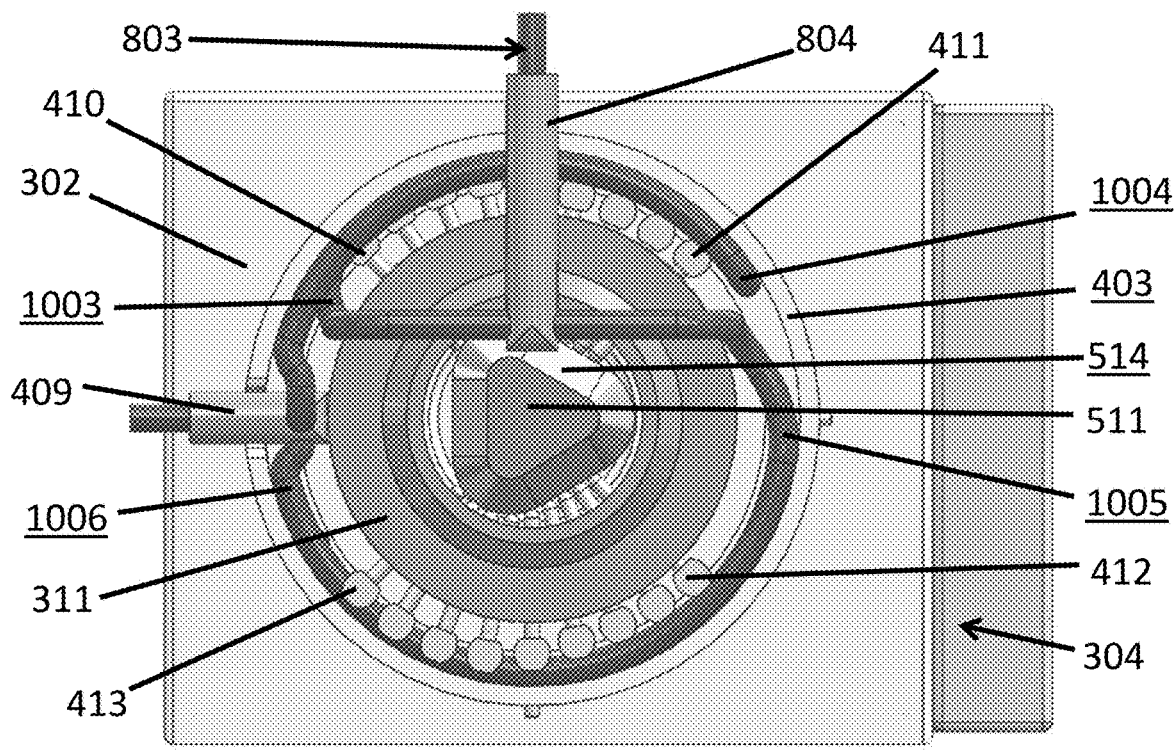
FIG. 19A Camshaft-Rotation is the front view of FIG. 18B.
Figure 19B:
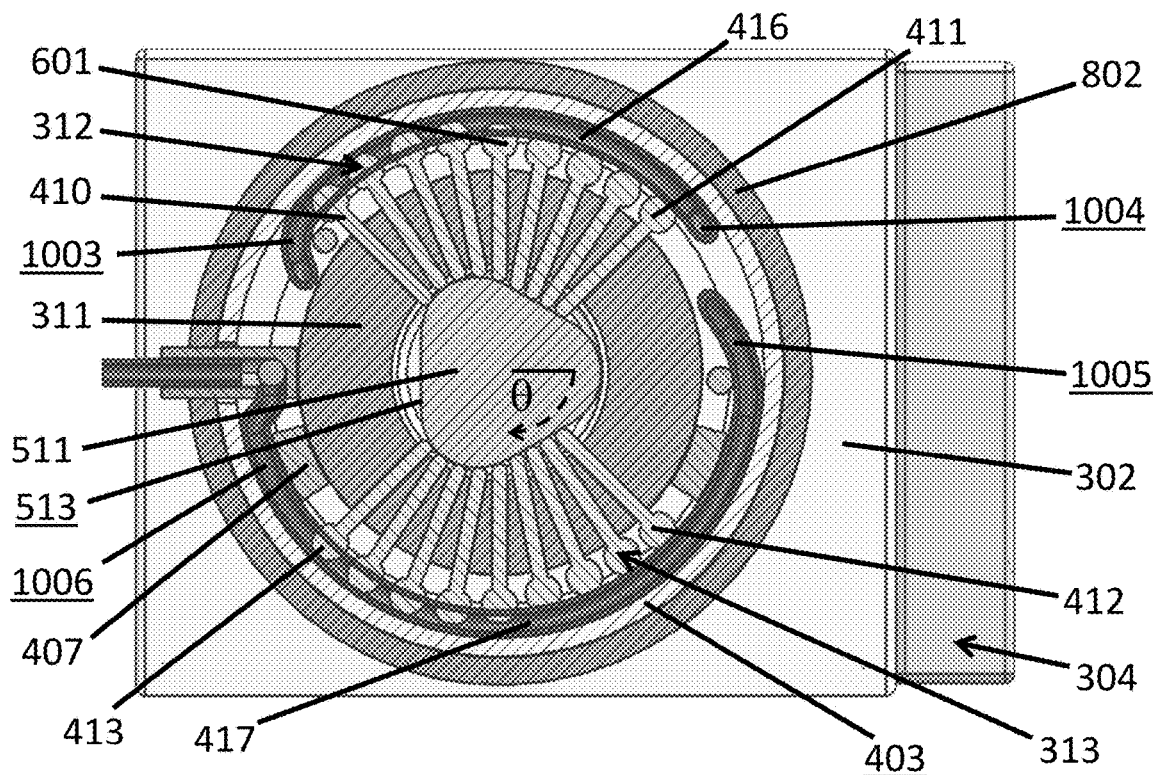
FIG. 19B cycle-home represents a cross-section of FIG. 19A as well as section C-C of Embodiment-A and equivalently Embodiment-B through Embodiment-F, portraying the interface between the critical components. Providing continuous flow output from all of the embodiments is described in FIG. 19B cycle-home through FIG. 24B.

Tube-section-1416 is the tube-section compressed by the cyclic compression from finger-set-1 312. Tube-section-2 417 is the tube-section compressed by the cyclic compression from finger-set-2 313. Tube-section-1416 and tube-section-2 417 are two parallel paths originating from the connector-input 804 and combined downstream at connector-output 409. Tubing-assembly-1408 and tubing-assembly-2 803 have an inlet and outlet as described. All of the embodiments shown typically provide flow in one direction for patient safety. FIG. 19B cycle-home through FIG. 23B describe the intricacies of the continuous flow Qout as a function of the camshaft-1511 rotation.

Embodiment-E

Figure 11A:
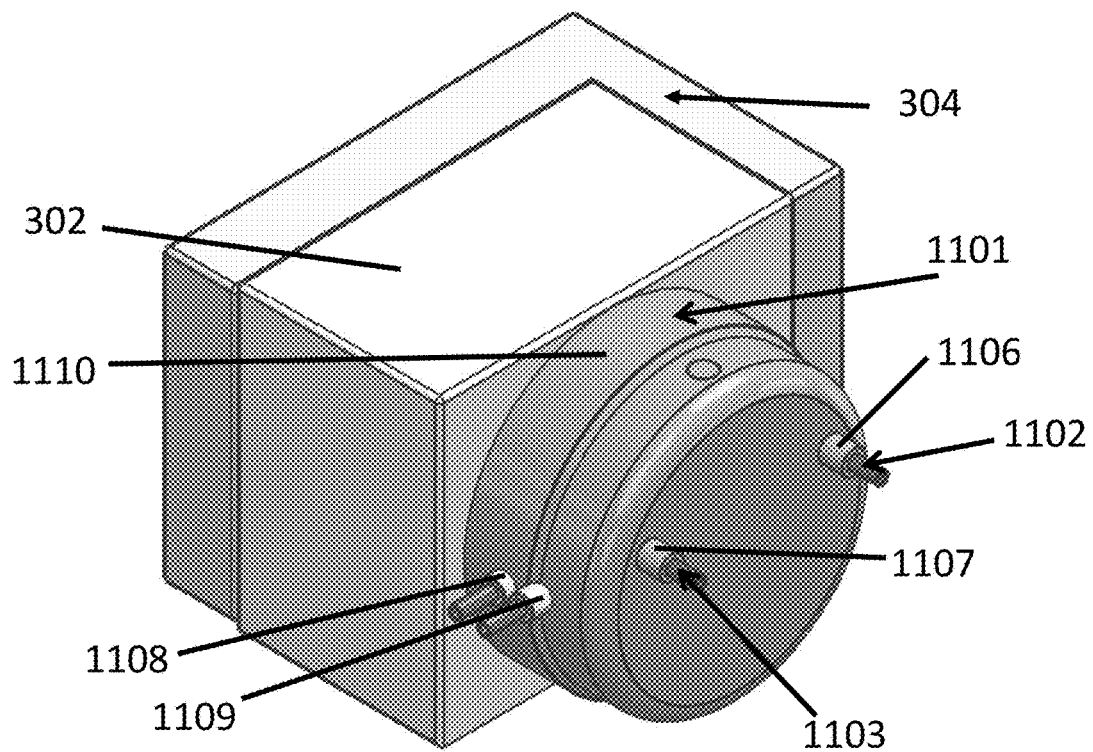
FIG. 11A Embodiment-E and FIG. 11B show the components of Embodiment-E.
Figure 11B:
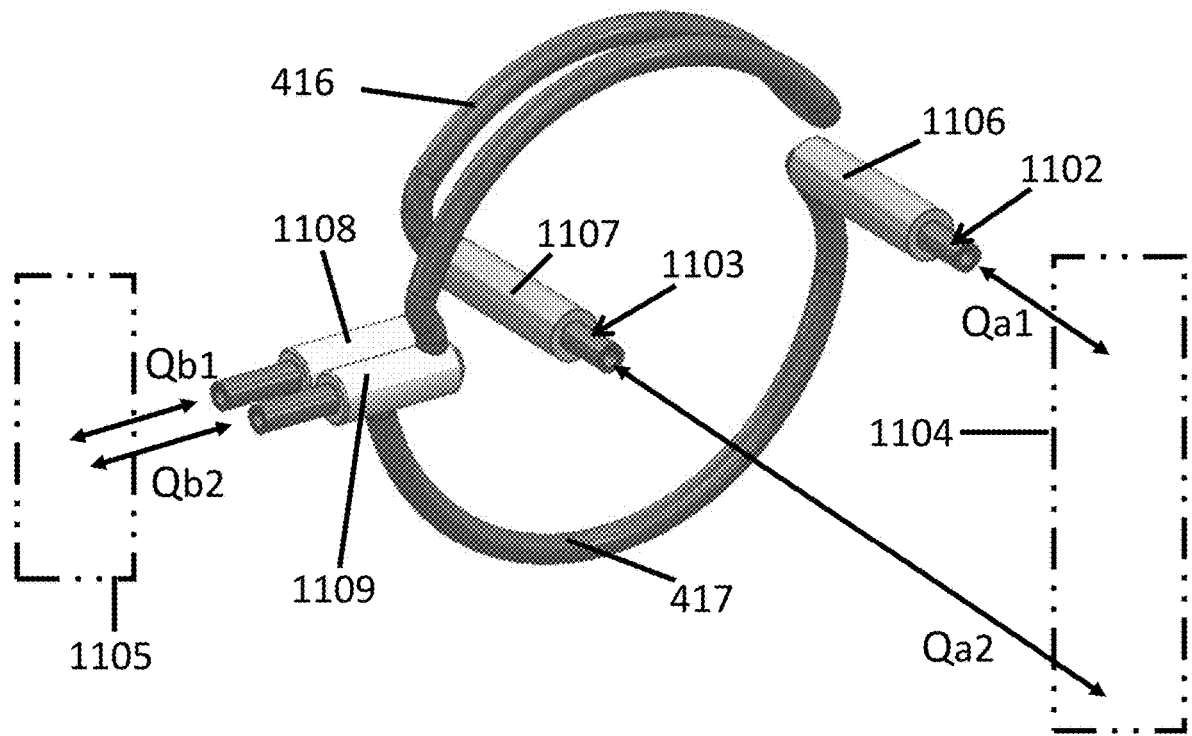

FIG. 11A Embodiment-E and FIG. 11B provide flow in both directions, dependent upon the direction of camshaft-1511 rotation. This embodiment, utilized for non-medical and some medical applications, can mix fluids and other non-liquid sources through the tubing. Cassette-assembly-E 1101 contains cassette-E 1110, tubing-E1 1102, and tubing-E2 1103. Flow Qa1 and Qa2 to and from environment-A 1104 occurs via connector-1*a* 1106 and connector-2*a* 1107. Flow Qb1 and Qb2 to and from environment-B 1105 occurs via connector-1*b* 1108 and connector-2*b* 1109.

FIG. 11B shows tubing-E1 1102 and tubing-E2 1103, as it would be oriented onto cassette-E 1110 and supported with the same tube-hold-1407 of all other embodiments. Tube-section-1416 is connected to connector-2*b* 1109 and to connector-2*a* 1107 whereas tube-section-2 417 is connected to connector-1*b* 1108 and to connector-1*a* 1106. Flows Qa1, Qa2, Qb1, and Qb2 can occur in both directions, dependent upon the direction of rotation of camshaft-1 511. Finger-set-1 312 operates throughout tube-section-1 416 and finger-set-2 313 operates throughout tube-section-2 417. The camshaft-1511 rotation determines the flow direction into and out of environment-A 1104 and environment-B 1105. This embodiment operates the same as FIG. 8A Embodiment-C as represented in FIG. 10D if environment-A 1104 included infusion-bag-external 1001 and if environment-B 1105 includes the infusion-patient 402. Another embodiment (not shown) would include the infusion-bag-internal 405. Similar to FIG. 3A Embodiment-A and FIG. 8A Embodiment-C, the tube-hold-1 407 isn't needed if the tubing-assembly-2 803 is inserted manually in the pump-assembly-1304. The combined output flow of Qa1 and Qa2 is continuous for a clockwise rotation of camshaft-1511. Similarly, the combined output flow from Qb1 and Qb2 is continuous for a counter-clockwise rotation of camshaft-1511.

Embodiments F and G

Figure 12A:
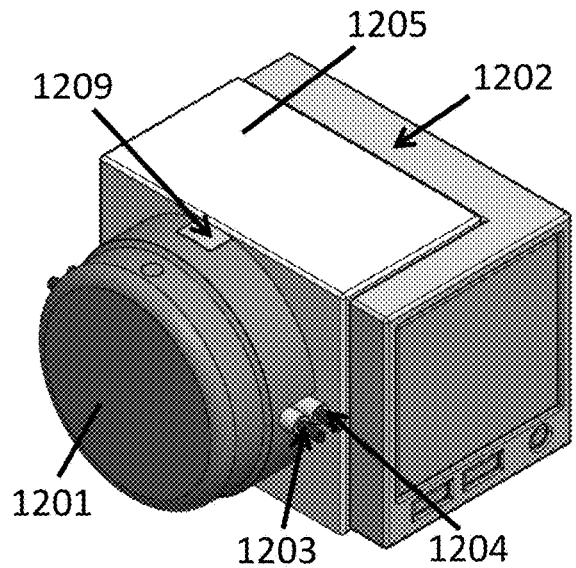
FIG. 12A Embodiment-F1 through FIG. 16 Embodiment-G4 show a different arrangement of the fingers to yield the same continuous flow output as the other embodiments.
Figure 12B:
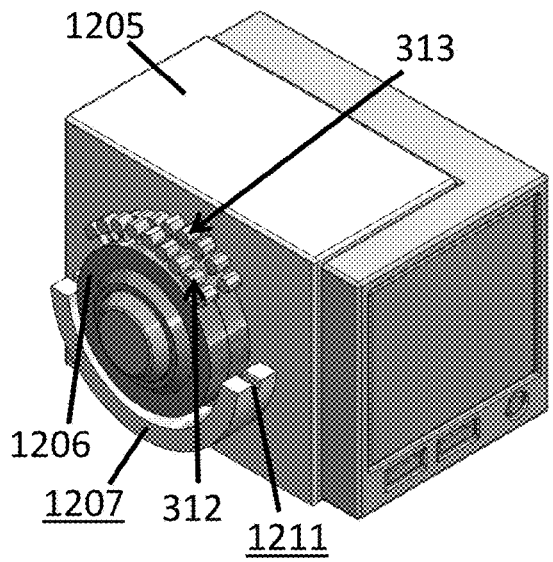

FIG. 12A Embodiment-F1 is similar to FIG. 11A Embodiment-E and all of the other embodiments with some changes to the implementation. Tube-hold-2 1209 protrudes from a section of cassette-F1 1201, providing the means of orienting tubing-F1 1203 and tubing-F2 1204, the tube-hold-2 1209 and cassette-F1 1201, onto base-3 1205 of pump-assembly-3 1202. Pushing the protrusion of tube-hold-2 1209 allows cassette-F1 1201 to be removed or installed, and it compresses the tubing-F1 1203 and tubing-F2 1204 to their proper operating mode. Tubing-F2 1204, shown behind tubing-F1 1203, has tubes exiting the cassette-F1 1201 on both sides. FIG. 12B is a perspective view of pump-assembly-3 1202. Base-3 1205 contains annular-flange-3 1207 as well as hold-groove 1211. The cylindrical opening of cassette-F1 1201 slips over the tube-hold-2 1209 and the annular-flange-3 1207. Sleeve-3 1206, similar to the upper half of other sleeves, has two sets of holes, with the second set directly behind the first set. The spacing between the holes of each set of holes is the same as the other sleeves. The sleeve-3 1206 accompanies finger-set-1 312 directly in front of finger-set-2 313.

Figure 12C:
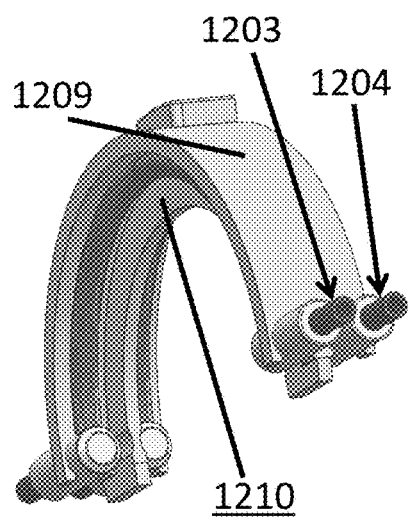
Figure 12D:
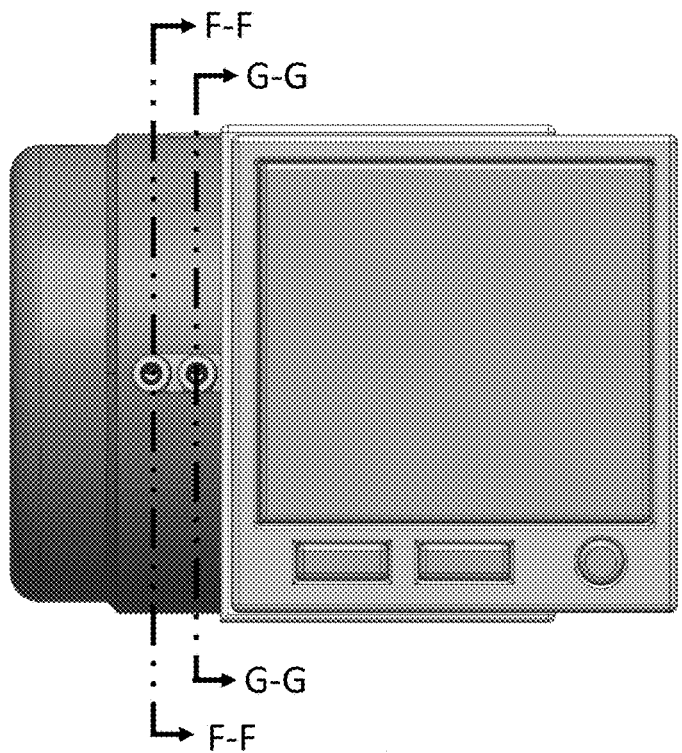

FIG. 12C is tube-hold-assembly-1 1208. Tube-hold-assembly-1 1208 contains tubing-F1 1203, tubing-F2 1204, and tube-hold-2 1209. The tube-hold-flange 1210 separates the two tube assemblies and becomes a support structure onto annular-flange-3 1207 once assembled with the cassette-F1 1201. The inner diameter of the tube-hold-2 1209, excluding the tube-hold-flange 1210 is the tube-seat for tubing-F1 1203 and tubing-F2 1204. Tube-hold-flange 1210 fits into hold-groove 1211 and straddles between finger-set-1 312 and finger-set-2 313. FIG. 12D is a front view of FIG. 12A Embodiment-F1. Section F-F and section G-G, described in FIG. 24A and FIG. 24B, describe how the continuous flow is the equivalent for all embodiments.

The removal and replacement for the tubing-F1 1203 and the tubing-F2 1204 can be either a new tube-hold-assembly-1 1208 or just replacing the tubing-F1 1203 and tubing-F2 1204. The cylindrical-opening surface of cassette-F1 1201 envelops both the tube-hold-2 1209 and annular-flange-3 1207.

FIG. 13A is the left-end view of FIG. 12D without the cassette-F1 1201 and cover 310. Tube-section-3 1301, part of tubing-F1 1203, is functionally equivalent to the tube-section-1 416 of all other embodiments. Camshaft-2 1303 has two cams, cam-f 1304 and cam-b 1305 each with the surface cam-profile 513. Angle-$\alpha_o$ is the angle between cam-f 1304 and cam-b 1305, matched with cam-profile 513 and the phasing between the two sets of holes of sleeve-3 1206. Angle-$\alpha_o$, shown at 60-degrees, is half of the cycle, which is 120-degrees. Cam-b 1305 aligned directly behind cam-f 1304 is effectively a single-cam separated with a groove.

The protrusion of tube-hold-2 1209 is pushed downward for cassette-F1 1201 installation and removal. Before pushing down the tube-hold-2 1209, there would be an interference between the tube-hold-2 1209 and the cassette-F1 1201. Positioning the tube-hold-2 1209 onto the annular-flange-3 1207 yields the tubing-F1 1203 and tubing-F2 1204 into the operational mode of yielding continuous output flow. Slipping the cassette-F1 1201 base-3 1205 locks the cassette-F1 1201 and tubing-hold-assembly-1 in place, allowing the downward force on tube-hold-assembly-1 1208 to be removed. The tube-hold-2 1209 could be attached directly with pump-assembly-3 1603 once the tube-hold-2 1209 is flush with annular-flange-3 1207. The compressive force of the tubing holds cassette-F1 1201 in place. A secondary lock (not shown) is optional. The tube-hold-assembly-1 1208, if contained by a secondary lock, would effectively be the embodiment's cassette. This embodiment wherein the tube-hold is the cassette (not shown) functions the same as the other embodiments except that the tubing interaction with the fingers is not covered, which would be acceptable in some non-medical applications.

FIG. 13B is a perspective view of several sub-components of FIG. 12A Embodiment-F1, yielding the rotary input to flow output. This arrangement of parts emphasizes the interface of the fingers, sleeve, and tubing placement with the drive-train, which controls the rotation of camshaft-2 1303. Tube-section-4 1302 is functionally the same as tube-section-2 417. Clockwise rotation of camshaft-2 1303 draws fluid flow Qa1 and Qa2 in from the left-end of FIG. 13A, and its output flow Qb1 and Qb2 is to the right. The combined output flow of Qa1 and Qa2 is a continuous output flow Qout for a clockwise rotation of camshaft-2 1303. The combined output flow of Qb1 and Qb2 is continuous output flow Qout for a counter-clockwise rotation of camshaft-2 1303. Tube-section-3 1301 is similar to tube-section-1 416 because both provide the clockwise fluid-flow path from finger-1*a* 410 to finger-9*a* 411 based on the clockwise rotation of camshaft-2 1303.

FIG. 13C shows a perspective view between the alignment of camshaft-2 1303 with the gear-camshaft 510. Cam-f 1304 has the same cam-profile 513 as camshaft-1 511, aligned with the recess of cycle-indicator 512 for each cycle of 120-degree locations. Cam-b 1305 also has the same cam-profile 513 as camshaft-1 511. The angle-$\alpha_o$, located midway between two of the cycle-indicator 512 recesses of gear-camshaft 510, is the value of cycle-home of 120-degrees divided by two or 60-degrees. The three cycle-home locations of the cam-profile 513 aligned with the cycle-indicator 512 of gear-camshaft 510. Similar to section C-C defined in FIG. 6A, the section lines of section F-F and section G-G defined in FIG. 12D yield the plane of action for finger-set-1312 and the second plane of action for finger-set-2 313, both set in position with the holes of sleeve-3 1206. The plane of action of each set of holes, established from the central axis of each set of holes, matches the cam-profile 513. The finger's central axis shares this same plane of action for each set of fingers.

Figure 14A:
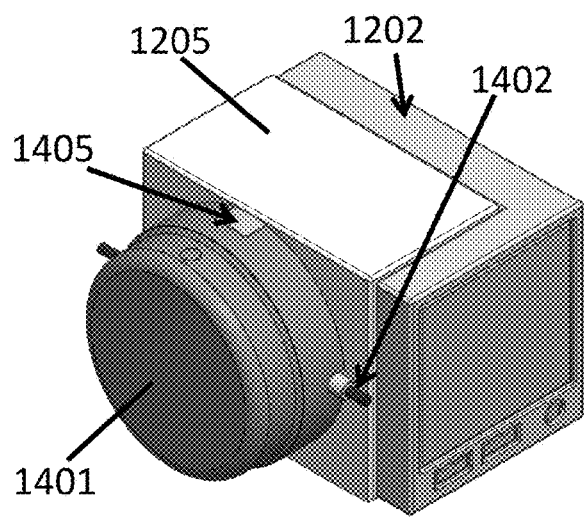
Figure 14B:
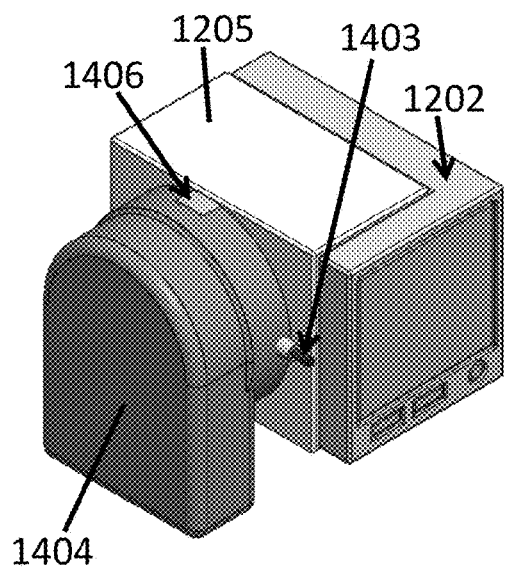

FIG. 14A Embodiment-F2 is similar to FIG. 12A Embodiment-F1, wherein cassette-F2 1401 has one input and output connector as part of tubing-FG1 1402. The output flow is continuous in either direction, dependent upon the camshaft-2 1303 angular rotation direction. FIG. 14B Embodiment-F3 is similar to FIG. 14A Embodiment-F2, wherein cassette-F3 1404 includes the internal infusion-bag-internal 405 with the tubing-FG2 1403. The F-embodiments incorporate the tube hold assemblies to hold and position the tubing and the cassettes to mate with the pump housings. Three additional embodiments incorporate the tube-hold parts within the design of the cassettes.

Figure 14C:
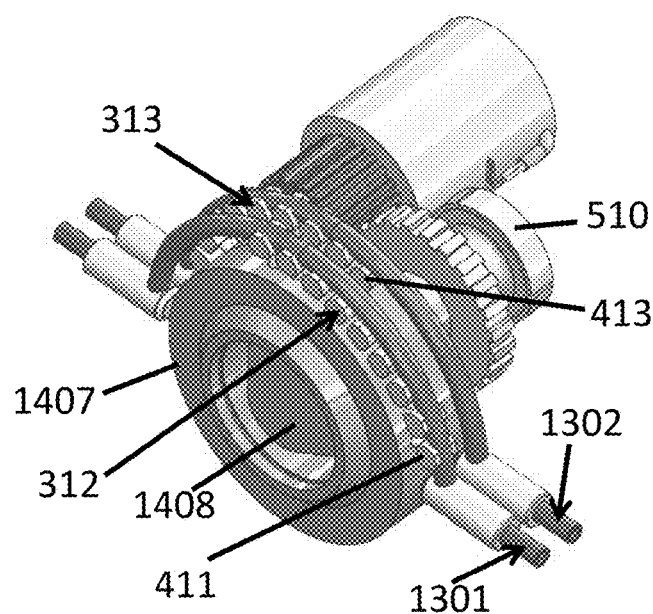
Figure 14D:
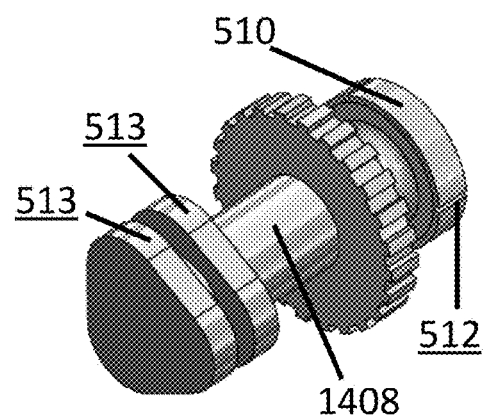

FIG. 14C is similar to the perspective view of FIG. 13B, showing the components to establish continuous flow output for a different camshaft. Sleeve-4 1407 has the back-set of holes phased at 60-degrees, wherein finger-9b 413 is oriented 60-degrees from finger-9a 411. FIG. 14D, similar to FIG. 13C, shows the arrangement of camshaft-3 1408, aligned with gear-camshaft 510. The difference is that camshaft-2 1303 has cam-b 1305 offset radially from cam-f 1304 whereas camshaft-3 1408, with angle-OW equal to 0-degrees, is effectively a single cam with an annular groove in the middle of the surface of the cam-profile 513. This groove accommodates the tube-hold-flange 1210.

Figure 15A:
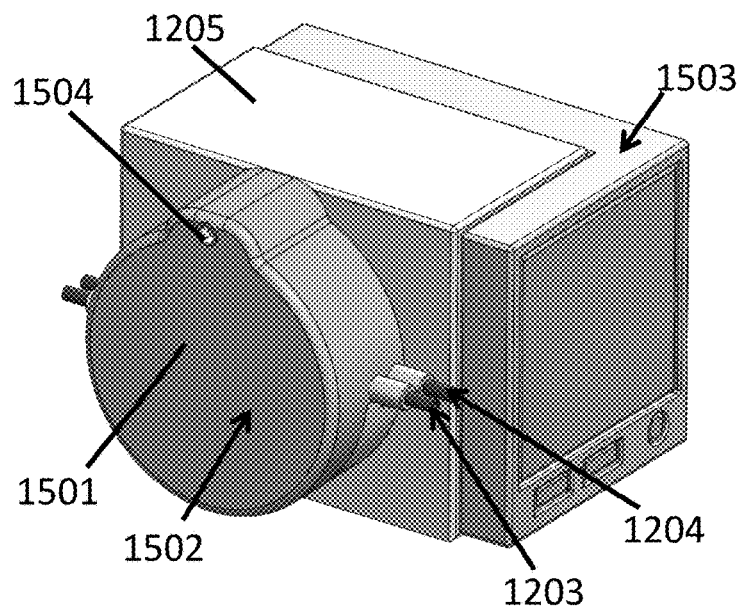
Figure 15B:
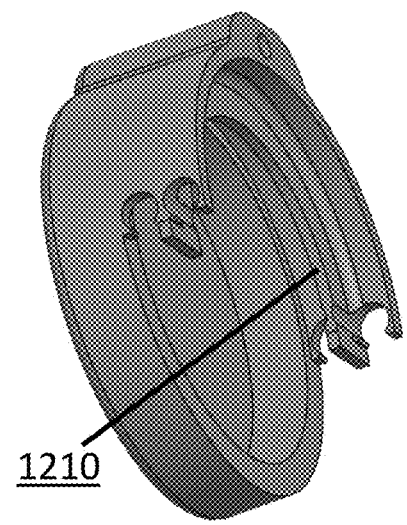
Figure 15C:
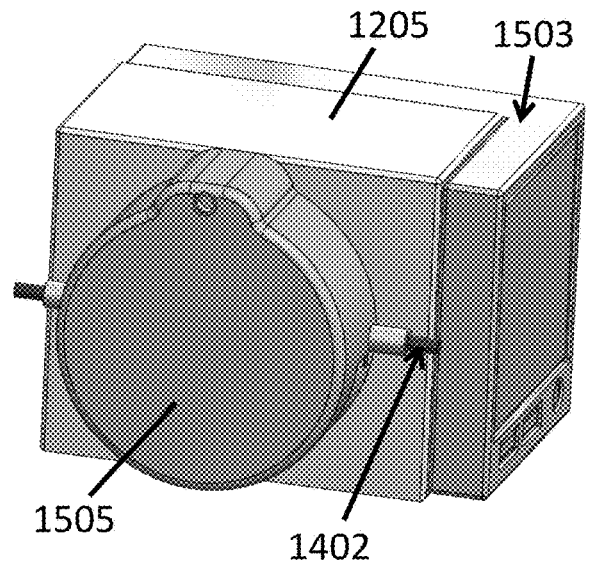

FIG. 15A Embodiment-G1 combines the tube-hold-2 1209 and cassette-F1 1201 into one part, cassette-G1 1501. Cassette-assembly-G1 1502 consists of cassette-G1 1501, tubing-F1 1203, tubing-F2 1204, and fastener-cassette 1504. Pump-assembly-4 1503 mates with cassette-assembly-G1. FIG. 15B is cassette-G1 1501. FIG. 15C Embodiment-G2 with cassette-G2 1505 is similar to FIG. 14A Embodiment-F2, and FIG. 15D Embodiment-G3 with cassette-G3 1506 is similar to FIG. 14B Embodiment-F3. There are several differences between the F-embodiments and the G-embodiments. First, the G-embodiments incorporate the tube-hold features within the design of the cassettes. Secondly, the angular position between finger-set-1312 and finger-set-2 313 differs between the F-embodiments and the G-embodiments. Thirdly, the F-embodiments utilize two cams, whereas the G-embodiments employ an effective single cam. The F-embodiments employ the angle-$\alpha_o$ equal to 60-degrees, whereas the G-embodiments utilize the angle-$\alpha_o$ of 0-degrees. Other embodiments (not shown) utilizing angle-$\alpha_o$ between the value 0-degrees and 60-degrees are matched with the proper phasing within the sleeve to yield continuous flow output. Similar to FIG. 14A Embodiment-F1, the cassette-assembly-G1 1502 is pushed downward onto annular-flange-3 1207 of base-3 1205 and locked into place with fastener-cassette 1504. This fastener could be a lever or a lever mechanism. FIG. 19A Cam-Rotation through FIG. 24B describes the equivalence of all twelve embodiments and the operation of obtaining continuous flow Qout. The conclusion section will also discuss the terms utilized, which effectively equate all of the embodiments to yielding the same continuous flow output common to all embodiments. All the pump-assemblies have a cylindrical bore that guides, becoming the bearing for the camshaft rotation.

Figure 15D:
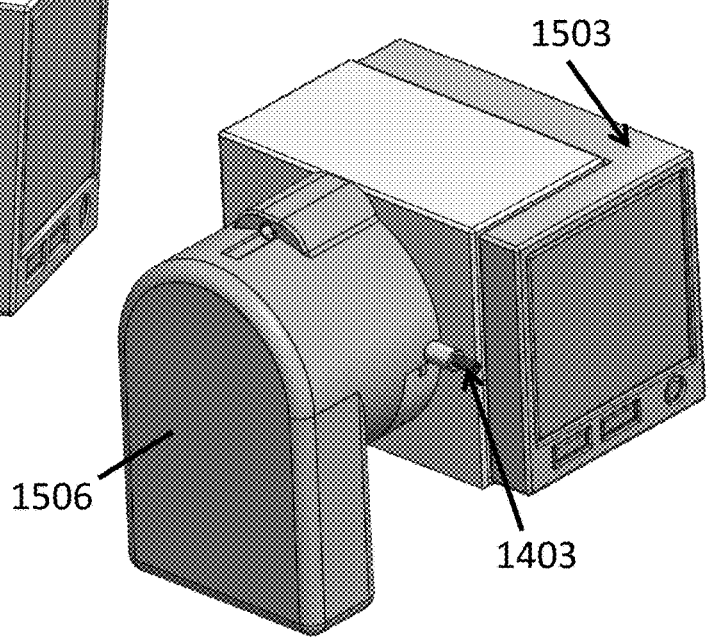
Figure 16:
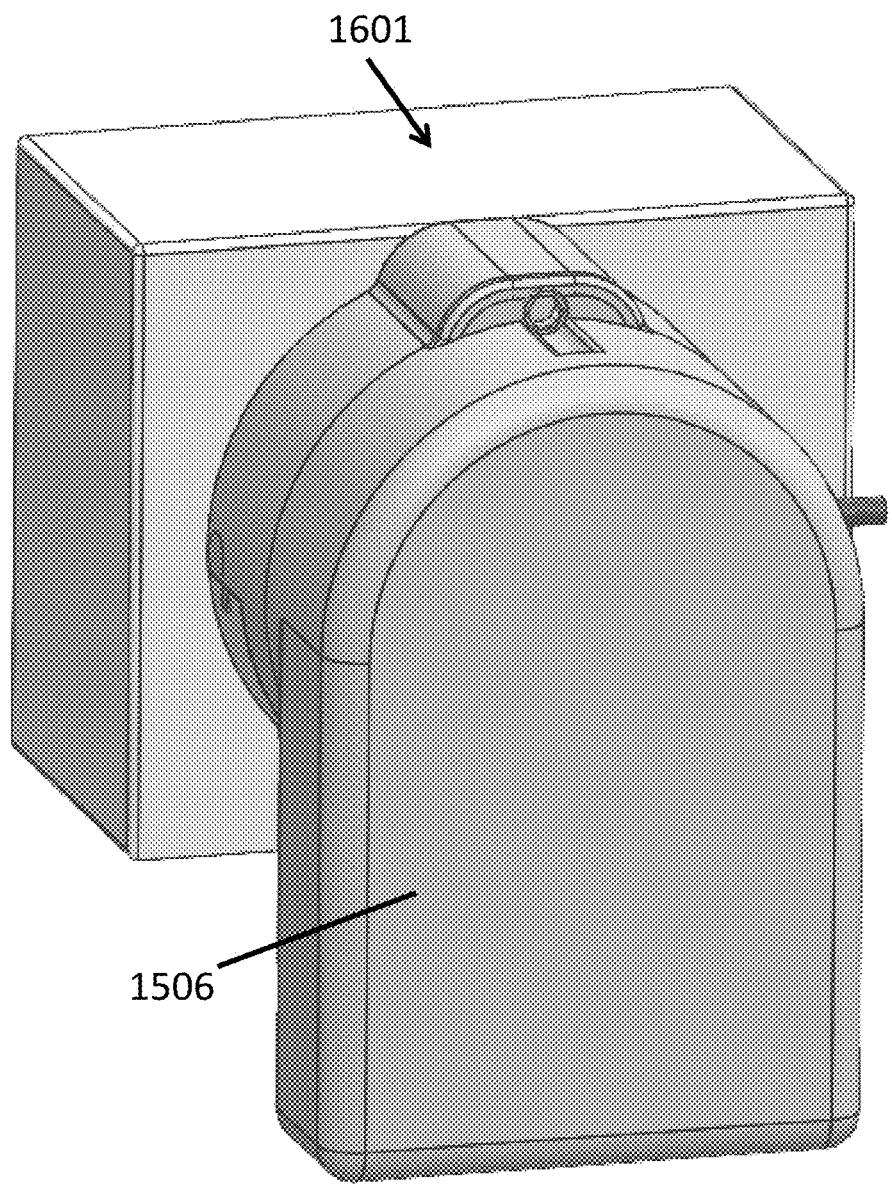
FIG. 16 Embodiment-G4 utilizes a mobile app to perform some of its functions.

FIG. 16 Embodiment-G4 utilizes pump-assembly-4 1606 with cassette-G3 1506, the same cassette utilized in FIG. 15D Embodiment-G3. Pump-assembly-4 1601 utilizes a mobile app to perform functions remotely, resulting in fewer parts. A mobile application such as a cell phone provides this embodiment's screen and shares the software. The resulting physical envelope of this embodiment is smaller than the other embodiments.

Finger-Retention Options

Figure 17B:
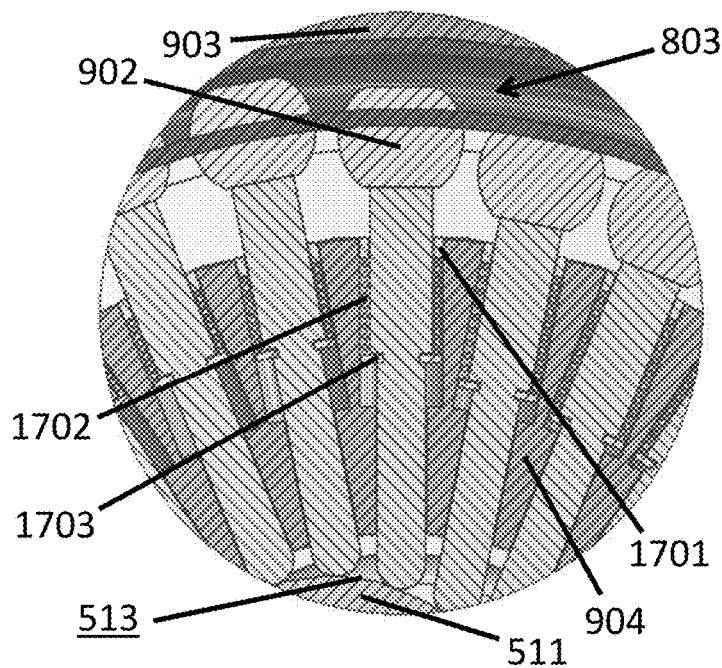
Figure 17C:
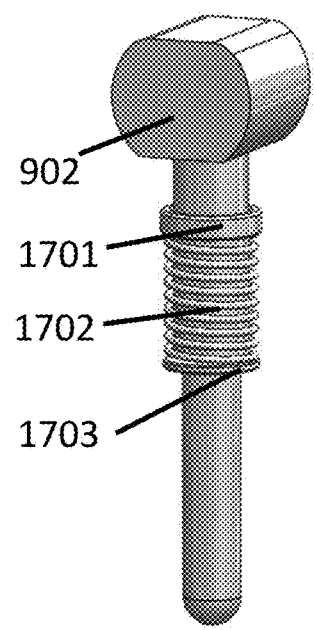

FIG. 17A through FIG. 17C show an option for finger retention utilized in FIG. 7A Embodiment-B and FIG. 9A Embodiment-D. These embodiments use the cassette-D 903 inner-diameter surface tube-seat to hold the tubing-assembly-2 803 against the finger action. FIG. 17A is section E-E defined in FIG. 9C of FIG. 9A Embodiment-D. FIG. 17B is section H-H defined in FIG. 17A. The fingers utilized in FIG. 17A through FIG. 17C use compression springs to keep the fingers within the sleeve-2 904 when either cassette-assembly-B 701 or cassette-assembly-D 901 is not attached. Spring 1702, held between the spring-stop 1701 and the spring-retainer 1703, applies a downward force keeping the finger-5c 902 in contact with the camshaft-1 511. The spring-stop 1701 shown in FIG. 17B is press-fit to the sleeve-2 904, providing a stop for spring 1702. The other end of spring 1702 pushes against spring-retainer 1703, allowing the force to load against the cam-profile 513 of camshaft-1511.

FIG. 17C shows finger-5c 902, spring-retainer 1703, spring 1702, and spring-stop 1701. This subassembly is placed into sleeve-2 904, as shown in FIG. 17A and FIG. 17B. Finger-5c 902 is used to press-fit the spring-stop 1701 into the sleeve-2 904 yielding an interference-fit. The spring-stop 1701 is kept flush with the outer cylindrical surface of sleeve-2 904 by the shape of finger-5c 902. This action will keep finger-5c 902 and all other fingers from compressing the tubing-assembly-2 803 during the removal of the cassette-assembly-B 701 or cassette-assembly-D 901, as shown in FIG. 25A Camshaft-Retraction-full through FIG. 26C.

Finger-5c 902 extends and retracts during camshaft-1511 rotation which changes the force of spring 1702, directed toward the central axis of the sleeve-2 904 and camshaft-1 511. Spring 1702 has an effective spring rate to keep the force of spring 1702 sufficiently sized such that the motor 502 will perform its function of compressing the tubing-assembly-2 803. These fingers' rotation operates in the same fashion described in FIG. 19B cycle-home through FIG. 24B. FIG. 25A Cam-Retraction-full through FIG. 26C describes the removal and installation of cassettes and tubing. Another means of finger-retention can include a membrane (not shown) between the fingers and the tubing. The following section describes the continuous-flow sequence, with or without finger retention.

Continuous-Flow Operation

Figure 18A:
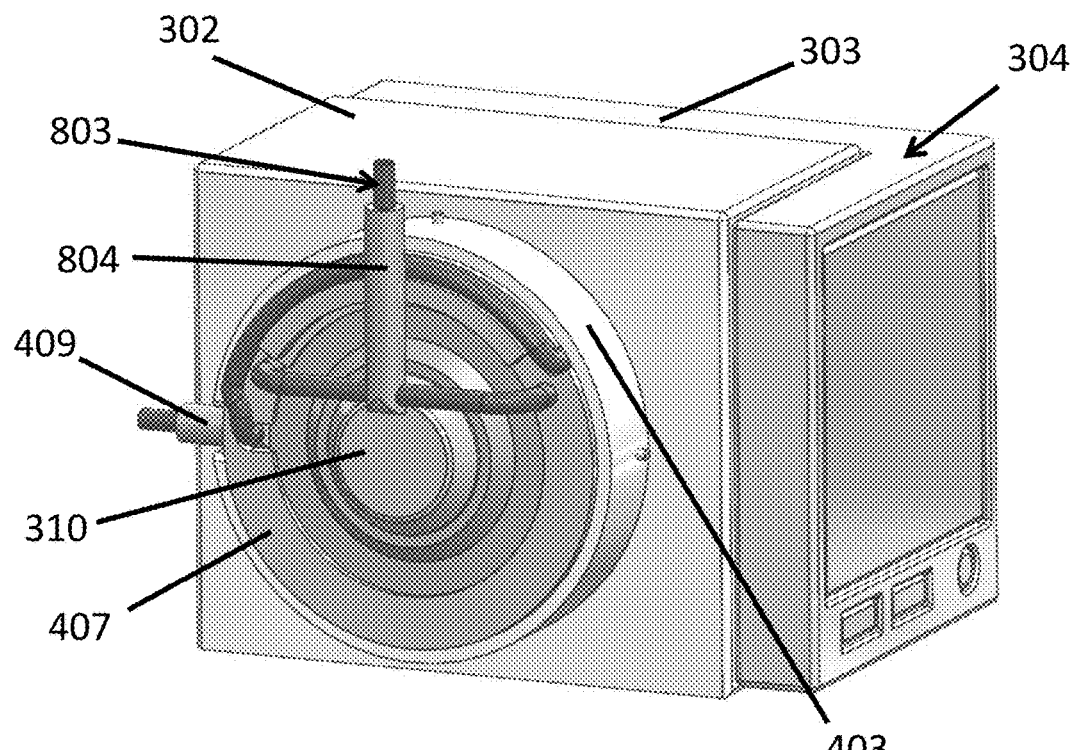
FIG. 18A shows a subassembly view of Embodiment-C.
Figure 18B:
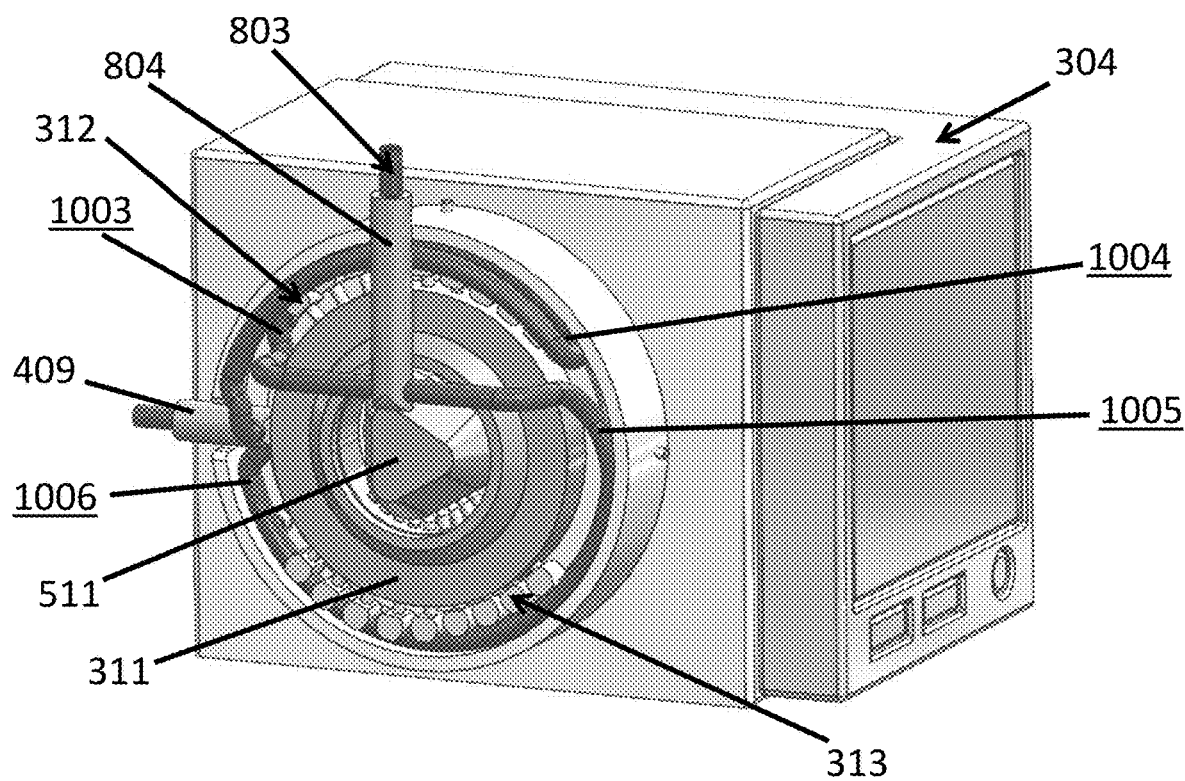
FIG. 18B is FIG. 18A without a couple of components to show some internal components.
Figure 23A:
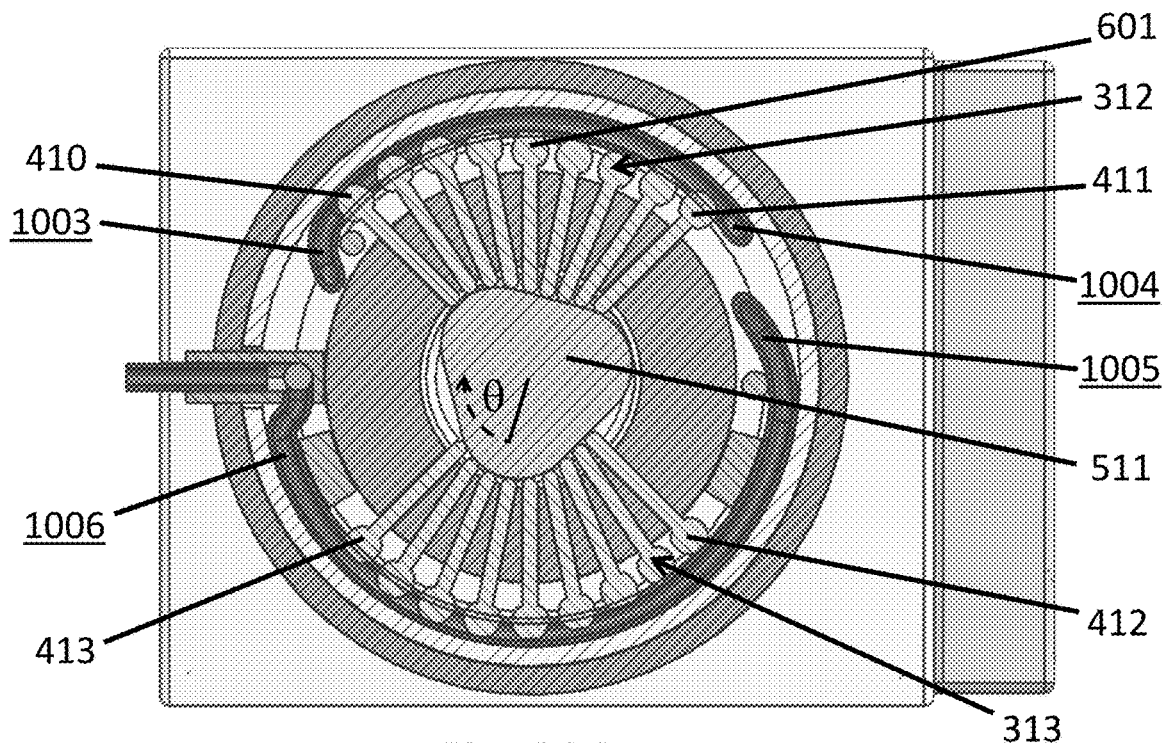
Figure 23B:
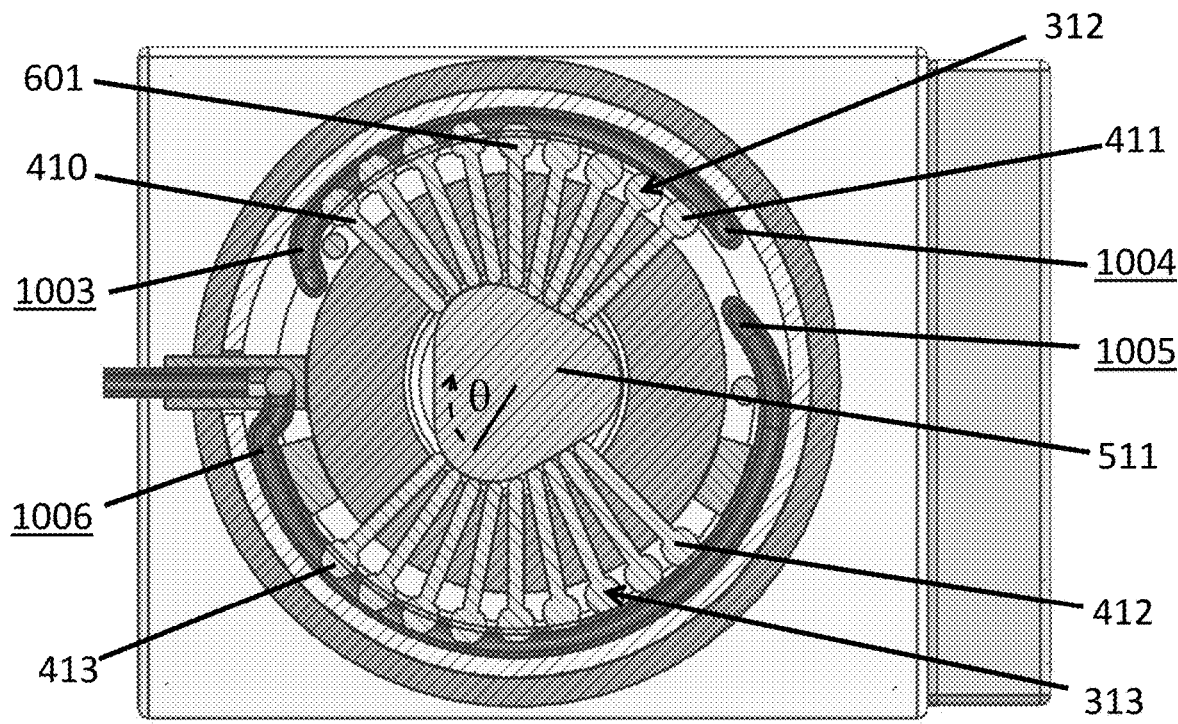
Figure 24A:
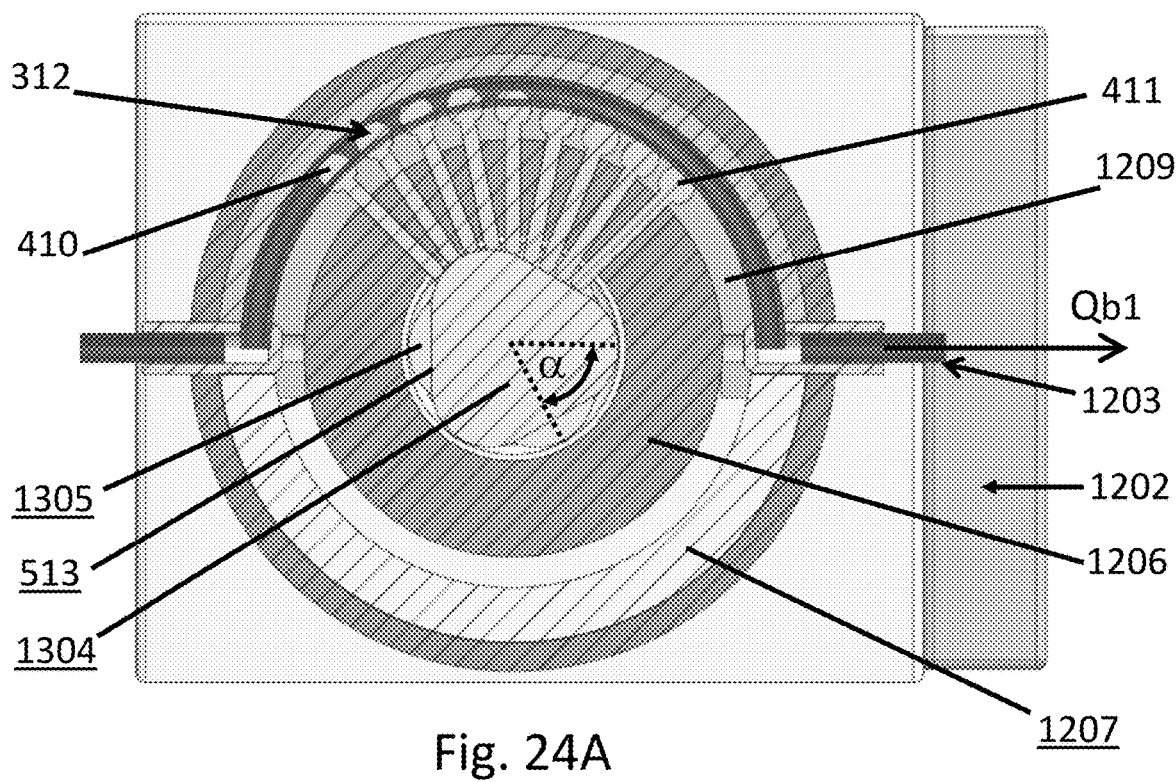
FIG. 24A through FIG. 24B show the operational equivalence of these embodiments.
Figure 24B:
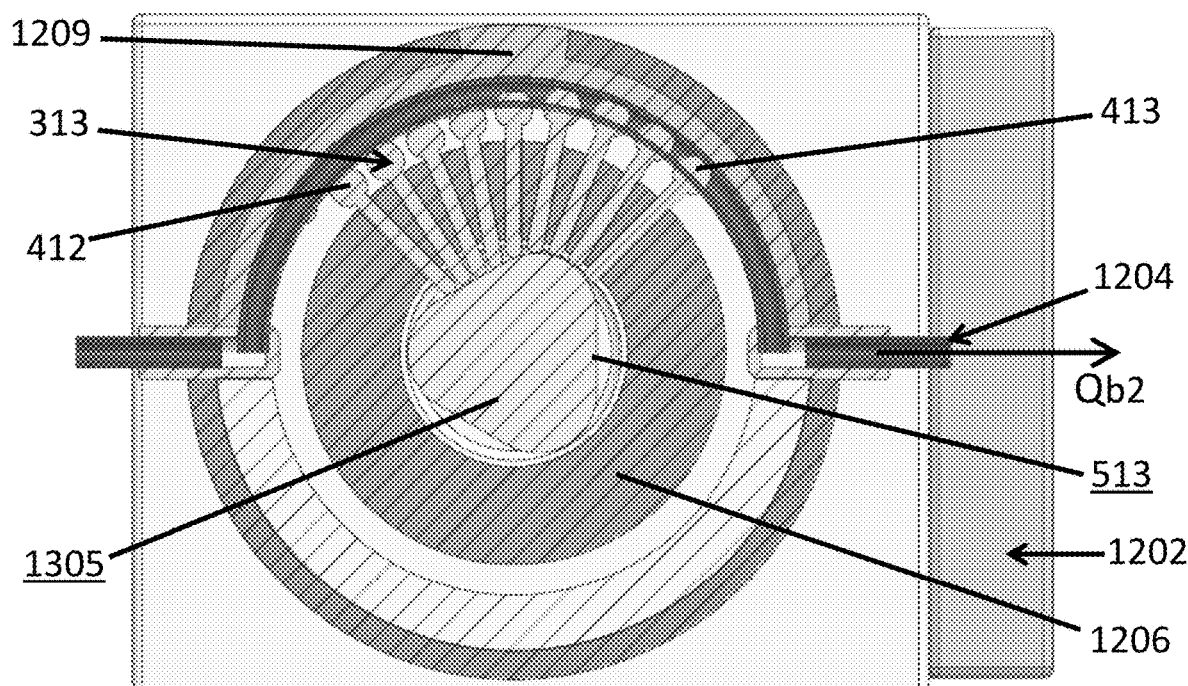
Figure 25A:
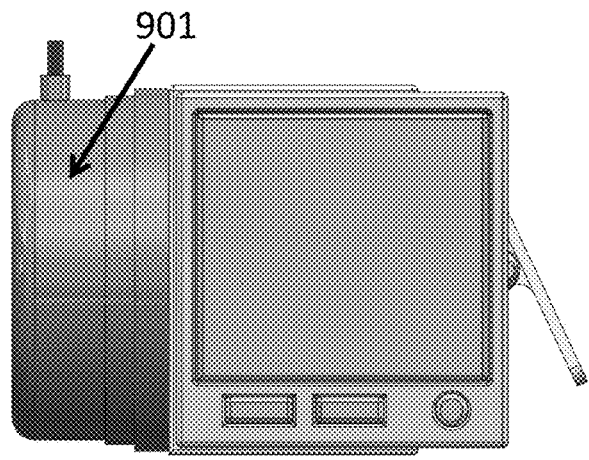
FIG. 25A Camshaft-Retraction-full through FIG. 26C portrays the assembly and disassembly of the cassettes and tubing assemblies for the five embodiments shown in FIG. 3A Embodiment-A through FIG. 11A Embodiment-E.

FIG. 18A through FIG. 24B describes how the continuous flow occurs for all embodiments. FIG. 12A Embodiment-F1, FIG. 14A Embodiment-F2, FIG. 1413 Embodiment-F3, and FIG. 15A Embodiment-G1 yield this same continuous flow utilizing a different arrangement of parts. FIG. 24A and FIG. 24B show how the F-embodiments yield continuous-flow output Qout. FIG. 18A is a perspective view of FIG. 8A Embodiment-C without cassette-C 802 to show the features of the tubing-assembly-2 803 with annular-flange-1 403 of base-1 302. FIG. 1813 is the same as FIG. 18A without the tube-hold-1 407 and the cover 310. FIG. 1813 shows finger-set-1 312 and finger-set-2 313, guided in place with sleeve-1 311. Finger-set-1 312 operates within tube-upper-in 1003 and tube-upper-out 1004. Finger-set-2 313 operates within tube-lower-in 1005 and tube-lower-out 1006. The flow of fluid goes through tube-section-1416 and tube-section-2 417, both connected to connector-input 804.

FIG. 19A is the left-end view of FIG. 1813 is equivalent to the pump-assembly-1 304 with tubing-assembly-2 803. FIG. 19B cycle-home is the sectional-view C-C defined in FIG. 6A. The clockwise angle θ shown in FIG. 19B, will explain the camshaft's rotation to yield continuous flow output Qout. The value θ is 0-degrees, matched with the cycle-home as monitored with the sensor-cycle 507. This cycle-home at 0-degrees also occurs at 120-degrees and 240-degrees rotation of the camshaft-1 511, occurring three times during one revolution of the camshaft-511. The cam-profile 513 of camshaft-1511 provides the surface for guiding all fingers compressing the tubing-assembly-2 803. The plane of the cross-section C-C of FIG. 6A shown in FIG. 1913 cycle-home yields the plane of action of camshaft-1511, including the cam-profile 513. The plane of action between the cam-profile 513, all of the fingers, and the tubing yield continuous flow output Qout.

Finger-set-1 312 and finger-set-2 313 are equally spaced, and each set of fingers spans 90-degrees. This span could also be 60-degrees or 120-degrees. The number of fingers can be more than nine for each set of fingers if the span of each set is 120-degrees. The number of fingers can be as little as four fingers depending on the span of each set of fingers. Cam-profile 513 sets the range of linear movement of all the fingers. The driving end of each of the fingers will cyclically pinch the tubing-assembly-2 803. The material properties of the tubing yield a resilient spring-like action keeping the fingers in contact with the cam-profile 513 of the camshaft-1511. The inner diameter of annular-flange-1, termed the tube-seat, supports the tubing assembly-2 803. The finger-set-1312 utilize tube-upper-in 1003 as the input flow region. The finger-set-2 313 uses tube-lower-in 1005 as the input flow region. Fluid flow is clockwise through tube-section-1416 from tube-upper-in 1003 to tube-upper-out 1004 and through tube-section-2 417 from tube-lower-in 1005 to tube-lower-out 1006. Upstream fluid flows through the upper-tubing region via the tubing sections starting from finger-1a 410 through finger-9a 411.

FIG. 19B cycle-home through FIG. 23B shows interference between the tubing-assembly-2 803, the tube-seat of annular-flange-1 403 the finger-set-1312, and the finger-set-2 313. The compression of the tubing is not displayed. The range of finger movement will push the thickness of the radial thickness of the tubing into the central tube fluid region, restricting the flow area. Once the thickness of the tube touches its other side thickness, the tube's cross-sectional area, and therefore flow, becomes zero. The central tube flow region, the lumen of the tubing, is sized with the finger linear displacement range to accompany the pump's full flow range. Compression of the tubing via the fingers distorts the lumen of the tubing. The shape of the finger-end compressing the tubing aids in controlling the flow continuity. FIG. 19B cycle-home through FIG. 23B describes the flow of fluid from tube-section-1416 and the tube-section-2 417 as a function of the rotation angle θ of camshaft-1511 clockwise rotation.

Figure 20A:
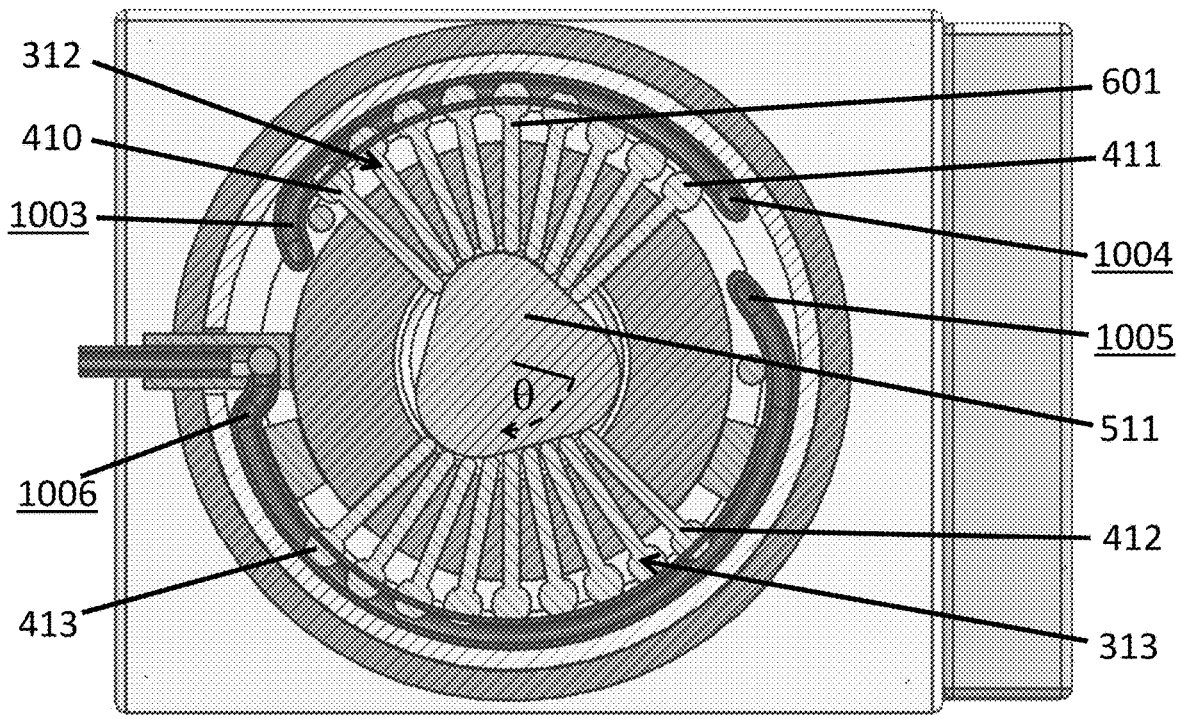
Figure 20B:
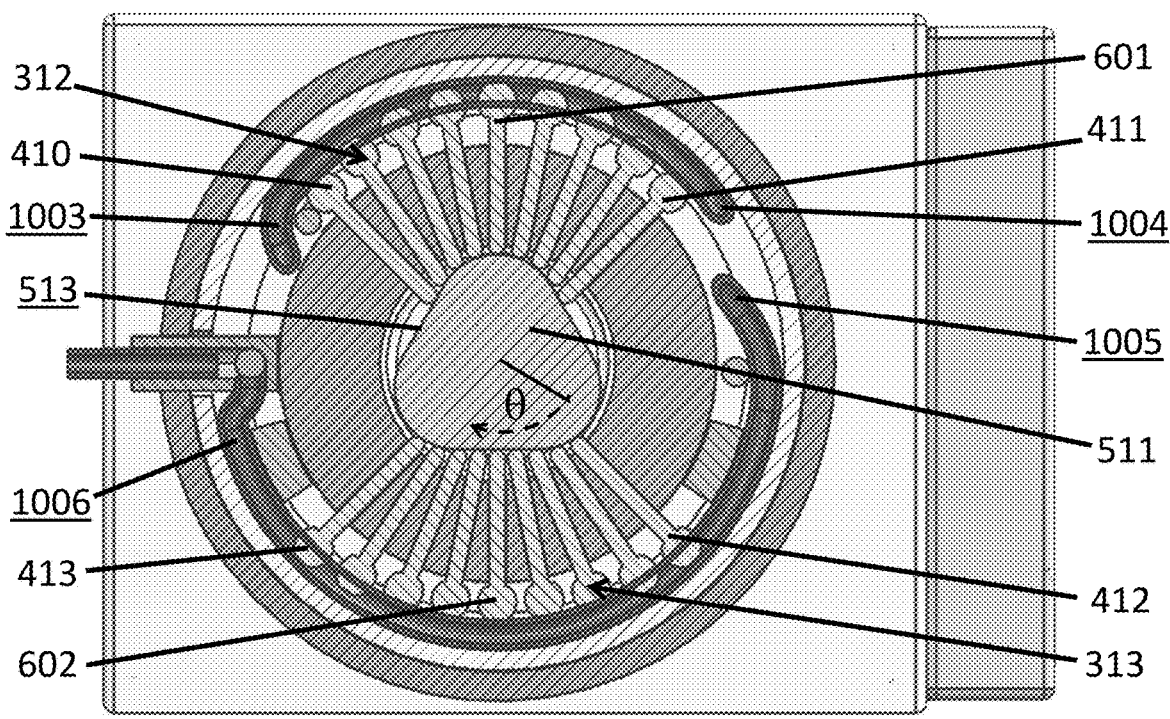

FIG. 20A shows the camshaft-1 511 rotated to θ of 15-degrees. Finger 1a 410 is starting to draw in the fluid from tube-upper-in 1003, whereas finger-1b 412 is finishing flowing fluid from drawing in from tube-lower-in 1005. The output flow through finger 9a 411 allows fluid to flow out tube-upper-out 1004 to connector-output 409, whereas finger-9b 413 does not yield flow output from tube-lower-out 1006 since it is closed off. The tube-seat for this embodiment is the surface of the inner diameter of annular-flange-1 403. Fluid is drawn through this lumen restriction because the distance between finger-1a 410 and the tube thickness at the tube-seat is more than the tube thickness. Distortion of the tube thickness occurs at finger-9b 413 to the size of a single tube thickness. The design of parts can accompany less compression as long as there is no open path throughout the lumen of tube-section-2 417. FIG. 20B shows the camshaft-1 511 rotated to θ of 30-degrees. The finger-set-1 312 provides full flow output, whereas the finger-set-2 313 is in its no-flow region.

Figure 21A:
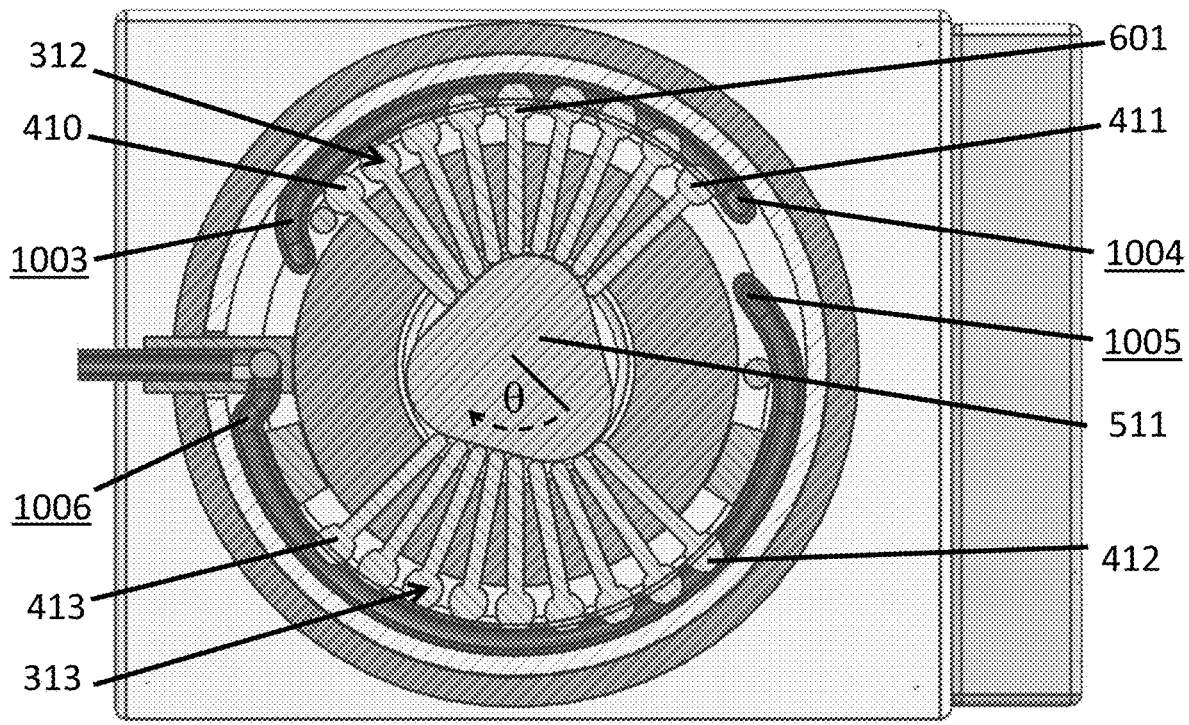
Figure 21B:
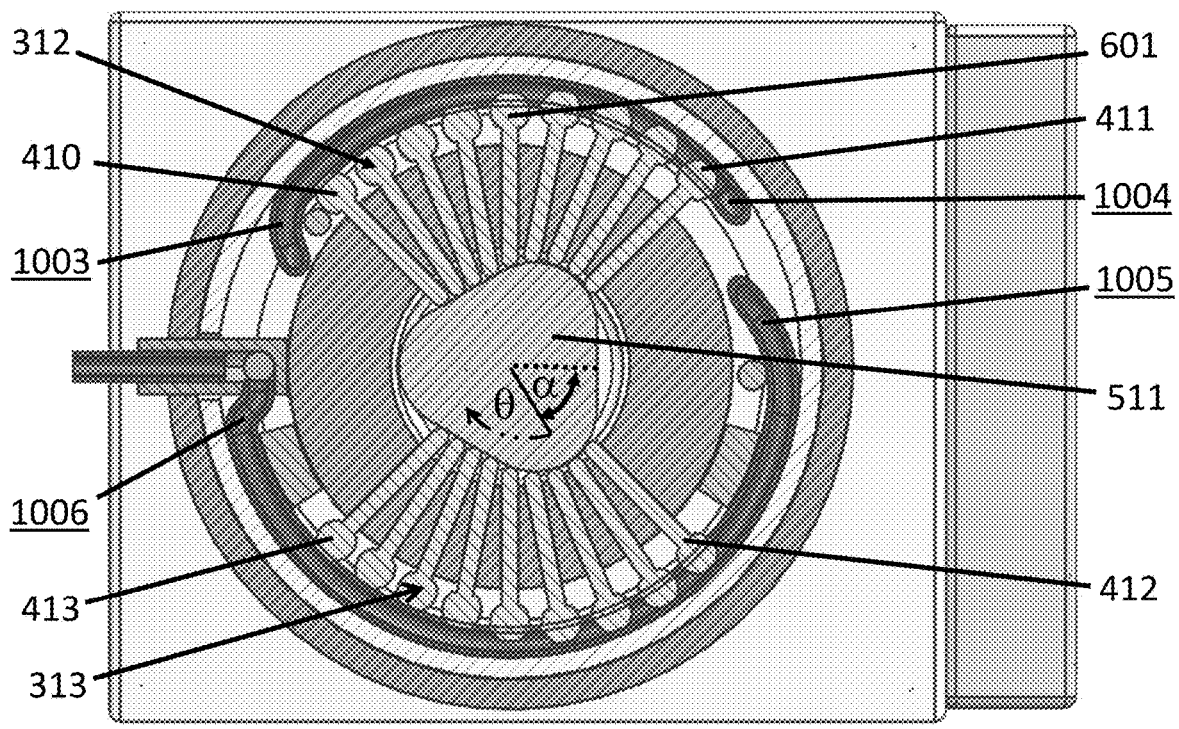

FIG. 21A shows the camshaft-1 511 at θ of 45-degrees. The finger-set-1 312 starts to shut off flow from finger-9a 411, whereas finger-9b 413 is just beginning to yield output flow. The flow is transitioning from the finger-set-1 312 and tube-section-1416 to the finger-set-2 313 and tube-section-2 417. This transition allows continuous flow output Qout as a function of camshaft-1 511 rotation. FIG. 21B shows the camshaft-1511 at θ of 60-degrees, wherein the flow has transitioned from finger-set-1 312 to finger-set-2 313. FIG. 21B also shows the angle-α equal to a cycle divided by two, equaling 60-degrees. The horizontal distance from the central axis of camshaft-511 and cam-profile 513 is the shortest, whereas the largest distance occurs at θ of 60-degrees. This range of radial distance to the cam-profile 513 yields the range of finger-translation for all of the fingers and defines the transition regions to yield continuous flow.

Figure 22A:
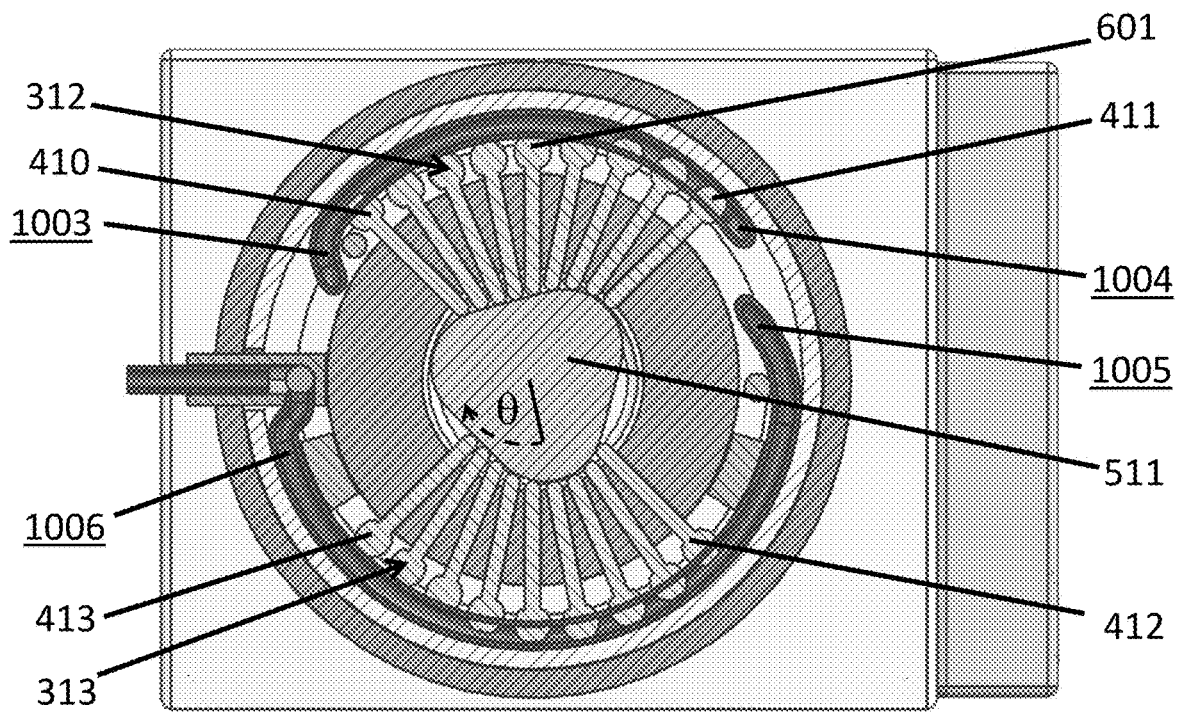
Figure 22B:
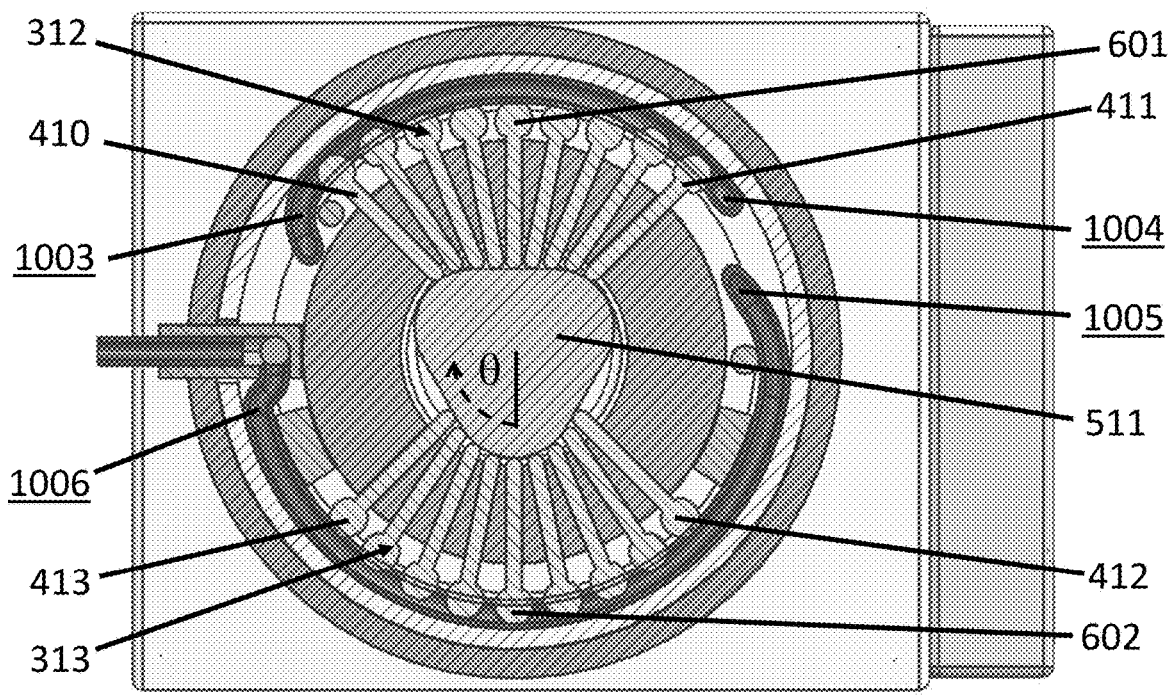

FIG. 22A shows the camshaft-1 511 at θ of 75-degrees. The output flow remains from finger-set-2 313, and the finger-set-1 312 remains without flow output from finger-9a 411. FIG. 22B shows the camshaft-1511 at θ of 90-degrees wherein the finger-set-2 313 is yielding full output flow while the finger-set-1 312 is in its no-flow region. This 60-degree camshaft-1 511 range, from θ of 30-degrees to θ of 90-degrees has switched the flow from tube-section-1 416 and finger-set-1 312 to tube-section-2 417 and finger-set-2 313.

FIG. 23A shows camshaft-1 511 rotation θ equal to 105-degrees which becomes the transition region of ending the flow from the finger-set-2 313 and starting the flow output from the finger-set-1 312. The opposite-transition-region creating flow from the finger-set-2 313 to ending the flow output from the finger-set-1312 occurred at θ of 45-degrees. Therefore, the difference between these transition regions is 60-degrees which is half of the cycle of 120-degrees. FIG. 23B shows the camshaft-1 511 at θ of 120-degrees, which is the same as FIG. 19B cycle-home. The flow output is now from the finger-set-1312, and the finger-set-2 313 does not yield flow output from finger-9b 413. The action of camshaft-1511 at 120-degrees is the same as the camshaft-1 rotation of 0-degrees, one of the three cycle-home locations.

The flow output Qout, which resulted from one cycle of the camshaft-1511 rotation of 120-degrees, is summarized as the combined output-flow Qout from both the tube-section-1416 and tube-section-2 417, doubling the volume output Vout of fluid from one of the sets of fingers. The phasing of finger-set-1 312 with finger-set-2 313, set by sleeve-1 311, matches the flow region of one set of fingers to the no-flow region of the other set of fingers yielding continuous flow output Qout. This combination yields the continuous flow from the connector-output 409 for one cycle of camshaft-1511 rotation. The volume output Vout for three cycles is triple the fluid volume of one cycle. The cam-profile 513, mated to the finger placement, yields the phasing between finger-set-1312 and finger-set-2 313. All embodiments yield continuous flow output Qout with volume output Vout proportional to the camshaft-1 511 rotation.

FIG. 24A is the cross-section F-F defined in FIG. 12D Embodiment F1; it also represents FIG. 14A Embodiment-F2 through FIG. 15D Embodiment-G3. The camshaft-2 1303 utilizes cam-f 1304 to control finger-set-1 312 to yield clockwise output flow Qb1 through tubing-F1 1203. FIG. 24B is section G-G of FIG. 12D. The camshaft-2 1303 uses cam-b 1305 to control the finger-set-2 313 to deliver clockwise output flow Qb2 through tubing-F2 1204. FIG. 12A Embodiment-F1 through FIG. 14B Embodiment-F3 mimics FIG. 3A Embodiment-A through FIG. 11A Embodiment-E to yield continuous flow output Qout. The equivalence of the single-cam camshaft-1511 with the two-cam camshaft-2 1303, phasing, angle-$\alpha_o$, and angle-$\alpha$ summarized for all embodiments in the conclusion section will show FIG. 12-A Embodiment-F1 through FIG. 15D Embodiment-G3 are equivalent to FIG. 3A Embodiment-A through FIG. 11A Embodiment-E to yielding continuous flow. Recalling that the G-embodiments are equivalent to the F-embodiments by rotating both the cam-b 1305 and the back-set of holes of sleeve-3 1206 counter-clockwise 60-degrees, the same is true for FIG. 24B describing the continuous output flow Qout. Rotating the cam-b 1305 and finger-set-2 313 counter-clockwise results in cam-b 1305 directly behind cam-f 1304, yielding an effective single-cam. This rotation also results in the proper phasing of 60-degrees, summarized in the conclusion section.

Cassette and Tubing Installation and Removal

Figure 25B:
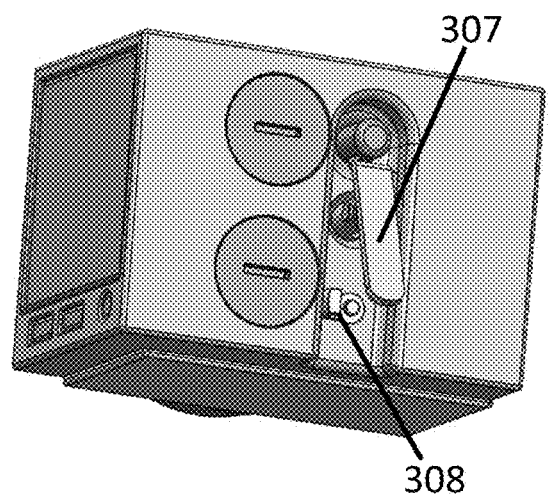
Figure 25C:
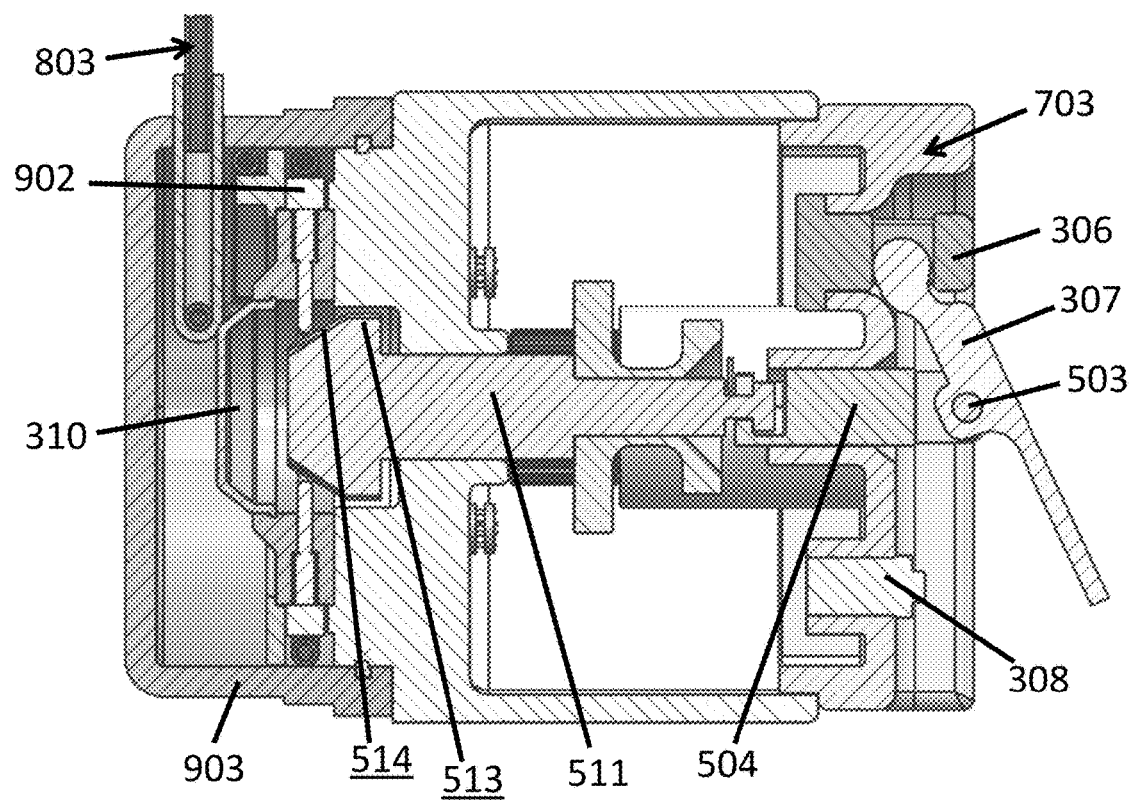

The cassette of FIG. 3A Embodiment-A through FIG. 11A Embodiment-E is removed by retracting the camshaft-1 511. The cassette of FIG. 12A Embodiment-F1 through FIG. 16A Embodiment-G4 utilizes a different means of removing or attaching a cassette. FIG. 25A Camshaft-Retraction-full is the same embodiment as FIG. 9A Embodiment-D. FIG. 25B shows the lever-assist 308 rotated clockwise 90-degrees and the lever 307 pulled outward. FIG. 25C is the same as section D-D showed in FIG. 9C, with the lever 307 rotated counter-clockwise. FIG. 25C shows the embodiment with the camshaft-1511 linearly translated longitudinally to the right resulting in the fingers sliding off the cam-profile 513 onto the surface of the cam-taper 514. The cam-taper 514 surface allows the fingers to move toward the central axis of camshaft-1511, relieving the tubing compression.

The plane of action, referenced in section E-E described in FIG. 9C, has changed concerning the position of the camshaft-1511. The plane of action has changed from the cam-profile 513 to the cam-taper 514 resulting in finger-5$c$ 902 removing the tubing compression. The Cassette-D 903 can therefore be removed and replaced. The initial locking of a given cassette to the mated base used in all embodiments, excluding the embodiments F and G, could include other options such as a set-screw (not shown). The lever 307 has a sliding pivot with lever-guide 306 and pin-pivot 503, allowing the lever 307 to rotate. The rotation of the lever pulls the camshaft-assist 504 to the right, as shown. The clevis-type-joint of camshaft-assist 504 switches from non-contact to pulling the right-end of camshaft-1511 when the pump is not in its operating status.

Figure 26A:
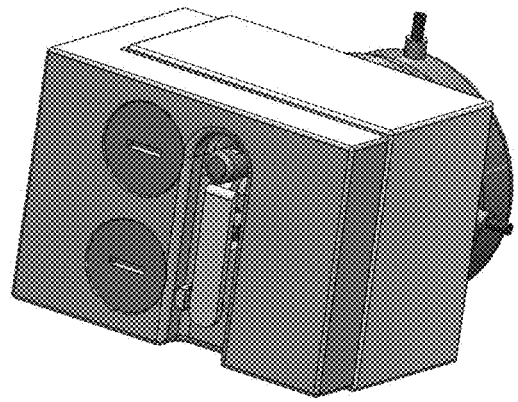
Figure 26B:
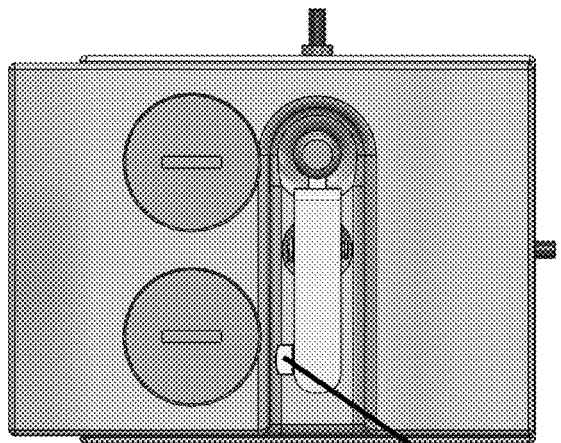
Figure 26C:
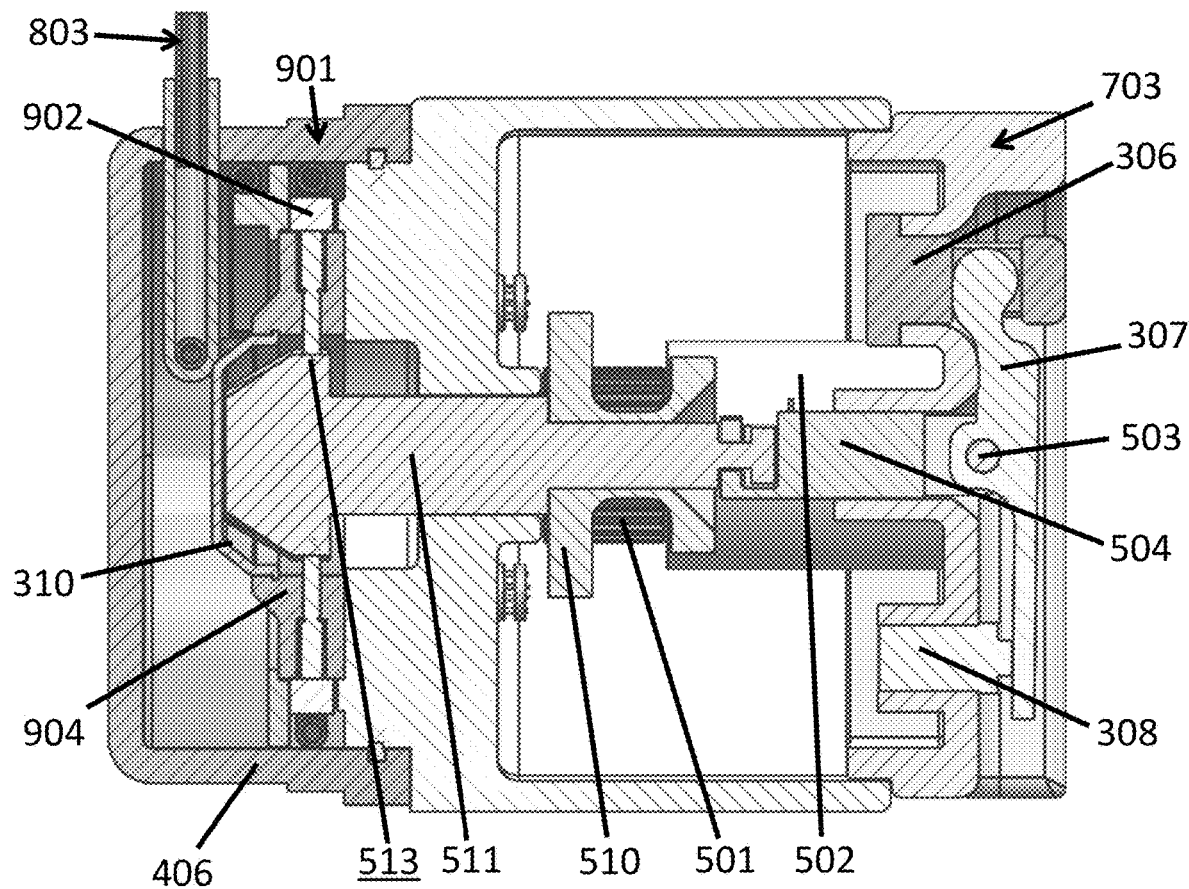

FIG. 26A Cam-Retraction-partial, FIG. 26B, and FIG. 26C show embodiment-D with camshaft-1 511 positioned to its operational mode. The cam-profile 513 of camshaft-1511 coincides with the plane of action with the sleeve holes, the fingers, and the tube-sections. The lever 307 is approximately 1-degree clockwise from its vertical position. The lever-assist performs a dual function, rotating and moving inward, parallel to the axis of camshaft-1511. Camshaft-assist 504 touches camshaft-1511, as shown. This contact will be relieved once the lever-assist 308 rotates the lever back to the pump's working position shown in FIG. 9C. Camshaft-1 511 of FIG. 9C is free to rotate because there is no contact between these parts due to the clevis-type joint of the camshaft-assist 504. The last step to keep the cassette-assembly-D 901 locked is to turn the lever-assist 308 back to its operational setting shown in FIG. 9C. The angular position of the camshaft-1511 does not affect the disassembly or assembly of cassette-D 903 or tubing-assembly-2 803.

FIG. 12A Embodiment-F1, FIG. 14A Embodiment-F-2, and FIG. 14B Embodiment-F3 utilize a different mechanism for removal and installation of cassette-F1 1201, cassette-F2 1401 and cassette-F3 1404. Once pushed down onto the annular-flange-3 1207, tube-hold-assembly-1 1208 allows the cassette-F1 1201 to be removed or replaced. Similarly, tube-hold-assembly-2 1405 and tube-hold-assembly-3 1406 allow cassette-F2 1401 and cassette-F3 1404 to be removed or replaced. This tube compression allows cassette-F1 1201, cassette-F2 1401, or cassette-F3 1404 to be either slipped onto or off the annular-flange-3 1207 and the corresponding tube-hold assembly. Unlike FIG. 3A Embodiment-A through FIG. 11A Embodiment-E, the tube-hold assemblies are assembled before the attached cassette, as described in FIG. 12A Embodiment-F1 through FIG. 14B Embodiment-F3. FIG. 15A Embodiment-G1 utilizes cassette-G1 1501, pushed down onto the annular-flange-3 1207 and then locked onto base-3 1205. FIG. 15A Embodiment-G1, unlike FIG. 12A Embodiment-F1, FIG. 14A Embodiment-F2, and FIG. 14B Embodiment-F3, has its tube-hold-2 1209 incorporated into the design of cassette-G1 1501. Similarly, the same is true for FIG. 15C Embodiment-G2, FIG. 15D Embodiment-G3, and FIG. 16 Embodiment-G4. All twelve embodiments utilize a common variety of features, terms, and definitions and two means of cassette and tubing installation and removal. A manual input directly to a camshaft (not shown) could include a hand-crank that would remove the motor and other components such as the electronics, software, and sensors.

CONCLUSION

All embodiments have a pump-assembly consisting of components that provide the rotary input means for the transmission of energy, yielding continuous output flow. All of these embodiments contain a pump-assembly with a bore for guiding the rotation of the camshaft. A given pump-assembly requires a cassette with tubing-assembly to mate with the pump-assemblies wherein the fingers control the compression of the tubing, yielding continuous flow output Qout. The rotary input means for the transmission of energy include the power source providing the ability of the electronics and software, the sensors and the output displayed on the screen, and other peripheral. The cam-profile 513 aligns with the plane of the sleeve holes and, therefore, the fingers of a given pump-assembly. A cassette can be as simple as a part to properly place the tubing and cover the pumping portions of the pump assembly. This cassette can also contain a tube-hold and house an infusion bag, typically utilized as the source of fluid for the pump. The tubing assembly includes two tube-sections, each compressed by the action of the fingers, and connectors for connecting tubing from a fluid source to a patient or other downstream functions. The tubing-assembly of a given embodiment contains the two tube-sections, the connectors, and the infusion-bag-internal 405 or the infusion-bag-external 1001, dependent upon the embodiment. The input and output regions of the tube-sections correspond to the tubing assembly's input and output, established by the direction of the camshaft rotation.

The sleeve orients the fingers to properly mate with the cam or cams of the camshaft. The holes of the sleeve are typically cylindrical. The sleeve has two sets of holes, each of which could be on the same or two parallel planes, dependent upon the embodiment. The holes are angularly equally spaced within each set of holes. A sleeve can also contain a counterbore for embodiments utilizing compression springs to retain fingers. Each hole of a given sleeve guides a finger which converts the rotary motion of the cam or cams and yields a translation of the fingers to compress the two tube-sections in a cyclic motion to yield the continuous flow. The position between the two sets of fingers, established with the sleeve's design, is critical to yielding continuous flow. Since each hole of a set of holes is equally spaced, the angular offset between the two sets of fingers is the phase-angle that controls the flow from one tube-section to the other, yielding continuous flow. The fingers are typically cylindrical with a radius end touching the cam of the camshaft and a shaped end compressing a tube-section. The end of the optional finger, which employs a spring-retention, has a larger cylindrical shape at the end in contact with the tubing.

The camshaft, driven by the rotary input means in the pump-assembly, contains one or two cams dependent on the sleeve design. Pumps utilizing the sleeve wherein the two sets of holes are on the same plane use the single cam. Pumps utilizing the sleeve wherein the two sets of holes are on parallel planes are accompanied by the double cam. Cams in each illustration utilize an outer surface based on two-dimensional geometry called the cam-profile 513 shaped as a regular-polygon over a given width of the cam with equal radii corners to control the transverse motion of all fingers. A regular-polygon is a polygon with equal-length sides and equal corner angles. In particular, the cam-profile is an equilateral triangle with equal radii corners. A cam-profile shaped as a square (not shown) with equal radii corners will also be summarized. The cam-profile describes the cycle as well as the cycle-home. The number of sides of a regular polygon's cam-profile establishes a pump's cycle. A cycle is equal to 360-degrees divided by the number of sides. The embodiments shown utilize a cycle equal to 120-degrees for the cam-profile 513 of an equilateral triangle. Cycle-home is a term defined by utilizing a sensor depicting a feature corresponding to a chosen reference angle of the camshaft of a given cycle. A given embodiment's continuous fluid flow output can use two-dimensional cam-profile geometry with its equivalent cam-profile surface generated over a given cam width interchangeably to describe the pump operation.

The fingers compress the tube-sections utilizing the tube-seat of a given embodiment as the holding function allowing the tubing compression created from the fingers. The tube-seat surface for the A, C, and E embodiments utilize the inner surface of the annular-flange-1403. The F-embodiments utilize the inner surface of the tube-hold-2 1209 as the tube-seat. The B, D, and G embodiments utilize the inner diameter of their cassettes to provide the tube-seat. The plane of the sleeve's holes establishes the plane of action of the fingers compressing the tube-sections. The single-cam pumps can alter this plane of action position regarding the camshaft's axial position during the cassette assembly and disassembly, including the tubing-assembly. For example, a lever mechanism can translate the single-cam camshaft to move from the surface of the cam-profile 513 to its adjacent and blended cam-taper 514. The cam-profile 513 and the cam taper 514 comprise the cam of camshaft 511. Once the axial translation reaches a given position, the fingers retract from the tube-sections, allowing disassembly of the tubing. These terms and definitions, expanded in the following summary of all embodiments, include the operation of the continuous flow and installing and removing the tubing and cassettes.

A continuous flow of medical fluid utilizing any of the twelve embodiments is ideal for a patient because it does not require fast cycling to avoid the peristaltic pump's anomalous, no-flow region. A disturbance to a prior art pump, potentially not detected and corrected until a cycle completes, can result in un-intended flow in the anomalous region or no flow in the flow region. FIG. 3A Embodiment-A through FIG. 11A Embodiment-E yields three cycles for a camshaft-1511 revolution. During one cycle, the flow transitions from tube-section-1416 to tube-section-2 417. The combined flow output Qout is continuous during a given cycle, and the volume output Vout is proportional to the angle θ of camshaft-1 511 rotation. These embodiments utilize tube-section-1416 and tube-section-2 417, and camshaft-1 511 with a single cam to yield continuous flow output Qout. FIG. 12A Embodiment-F1 through FIG. 16 Embodiment-G4 utilize tube-section-3 1301, tube-section-4 1302, and the dual-cams to obtain continuous flow output Qout.

All the embodiments utilize two tube-sections, meaning they both have an input and output typically combined as one input and one output. For example, FIG. 4A through FIG. 4D, FIG. 10A through FIG. 10D, and FIG. 1913 cycle-home describe the continuous-flow operation via tube-section-1416 and tube-section-2 417. Tube-upper-in 1003 combines with tube-lower-in 1005 of connector-input 804 as the input from the fluid source. Similarly, tube-upper-out 1004 and tube-lower-out 1006 combine downstream via connector-output 409 to provide continuous flow output Qout. FIG. 1913 cycle-home shows the camshaft-1511 at θ of 0-degrees, tube-sections and tube-regions, and both sets of fingers. Finger-set-1 312 operates within tube-section-1 416 and finger-set-2 313 operates within tube-section-2 417. The finger-set-1 312 is in its flow-providing mode, whereas finger-set-2 313 does not provide output flow or allow input flow. The terms and features cam-profile, phasing, cycle, cycle-home, tube-seat, and angle α will accompany this summary. For example, the phasing of finger-set-1312 with finger-set-2 313, set by the design of sleeve-1311, matches the flow region of one set of fingers to the no-flow region of the other set of fingers yielding continuous flow output Qout.

A simple means of describing the term phasing, or phase-angle, between finger-set-1312 and finger-set-2 313 is the angular difference between the most downstream finger-9*b* 413 of tube-section-1 416 and the most downstream finger-9*a* 411 of tube-section-1416 is 180-degrees. The most downstream finger determines fluid flow from its tube-section as witnessed throughout FIG. 1913 cycle-home through FIG. 24B, representing one cycle of camshaft-1 511 or camshaft-2 1303 rotation. One cycle of camshaft-1511 rotation is dependent on the shape of the surface cam-profile 513 utilizing the single-cam camshaft-1511. Cycle-home, equal to a cycle of 120-degrees and coinciding with each corner radii of the cam-profile 513, is monitored with sensor-cycle 507. Gear-camshaft 510 and its cycle-indicator 512, mated with camshaft-1511, link the software's control logic, electronics of board-main 509 of pump-assembly-1 304.

The cam-profile 513 is an equilateral triangle with equal radius corners. Therefore, one cycle is 360-degrees divided by the number of sides yielding 120-degrees. The angle-α is half of the cycle equally 60-degrees. This half-cycle of 60-degrees represents the flow region or no flow region of finger-set-1312 and finger-set-2 313. This half-cycle also defines the finger translation range for all fingers. The phase-angle between finger-set-1 312 and finger-set-2 313 of FIG. 3A Embodiment-A through FIG. 11A Embodiment-E is the value of a cycle of 120-degrees plus angle-a, totaling 180-degrees. Since there are three cycles for a given rotation, the volumetric amount of fluid Vout for one camshaft revolution is triple the amount of fluid for one cycle of rotation. If the cam-profile were a square with equal radii corners, the cycle would be 360-degrees divided by four, yielding 90-degrees and four cycles for a given camshaft rotation. The resulting angle-α would be the cycle divided by two or 45-degrees, and the phasing would be the cycle plus the angle-α yielding 135-degrees. A cam-profile consisting of five equal sides with equal radii corners would utilize fewer fingers due to limited physical space.

FIG. 3A Embodiment-A through FIG. 11A Embodiment-E utilizes parallel paths of tube-section-1 416 and tube-section-2 417 on the same plane as the plane of action of the holes of sleeve-1311 or sleeve-2 904. FIG. 12A Embodiment-F1 through FIG. 14C Embodiment-F4 utilize the parallel paths of tube-section-3 1301 and tube-section-4 1302 on parallel planes behind each other.

Although the resulting continuous flow is the same, FIG. 12A Embodiment-F1 is constructed without finger-set-2 313 in the same plane as the cam-profile 513. Instead, finger-set-2 313 is behind finger-set-1 312 as shown in FIG. 13B.

Two comparisons will portray the equivalence of the single and dual cam embodiments. First, compare FIG. 19B cycle-home with FIG. 24A and FIG. 24B and note that the tube-compression-profile of finger-set-1 312 of FIG. 19B cycle-home is the same as finger-set-1 of finger-set-1 of FIG. 24A. Note also that the orientation of cam-profile 513 of FIG. 19B cycle-home is the same as the cam-profile 513 of cam-b 1305 of FIG. 24B. Visualizing FIG. 19B cycle-home rotated counter-clockwise 180-degrees, the tube-compression-profile finger-set-2 313 is the same as the profile of finger-set-2 of FIG. 24B. Likewise, the cam-profile 513 of camshaft-1511 rotated 180-degrees is the same as the orientation of the cam-profile 513 cam-b 1305 of FIG. 24B. Secondly, compare FIG. 19B cycle-home, FIG. 21B, FIG. 24A, and FIG. 24B. Once again, finger-set-1 312 of FIG. 19B cycle-home yields the same tube compression profile as FIG. 24A. FIG. 21B shows the tube compression profile of camshaft-1 511 rotation of a half-cycle of 60-degrees which is the angle-$α_o$. The tube compression profile in FIG. 21B is the same as in FIG. 24B. Both of these examples show the equivalence of the dual-cam and single-cam embodiments.

FIG. 13A describes cam-b 1305 offset from cam-f 1304 by angle-$α_o$ of a half-cycle of 60-degrees. Angle-$α_o$ is the angle between cam-f 1304 and cam-b 1305, matched with cam-profile 513 and the phasing between the two sets of holes of sleeve-3 1206. Angle-$α_o$, shown at 60-degrees, is half of the value of the cycle. FIG. 15A Embodiment-G1 through FIG. 16 Embodiment-G4 would utilize angle-$α_o$ set to 0-degrees accommodated with a phase-angle of 60-degrees. Cam-b 1305 aligned directly behind cam-f 1304 is effectively a single-cam separated with a groove. The total radial span of both finger-set-1 312 and finger-set-2 313 would be the original span of 90-degrees plus the phase-angle of 60-degrees totaling 150-degrees. The tube-hold or cassette utilized can be installed by pushing downward because the total span of 150-degrees is less than 180-degrees, which is necessary for cassette installation and removal. The tubing must have the ability to be un-installed as well as installed on a given pump. The tubing of any assembled pump cannot be removed or installed until there is no compression of the tubing.

Cassettes, utilized in all embodiments described, mate and cover the tubing with the pump-assembly. Cassettes have holes or partial holes for containing the tubing and attaching to the pump-assembly and, in some embodiments, function as the tube-seat. All cassettes have a central axis which, when assembled to its mated pump-assembly, aligns with the bore of the pump-assembly. The access-hole to the cassette is a typically cylindrical or partial cylindrical shape from its central axis. This access-hole leads into an internal chamber of which the size and shape accommodate the tubing assembly and internal infusion bag if utilized. The goal of removing and installing cassettes and tubing from the pump-assembly is to avoid disturbing the tubing placement via two methods. First, FIG. 3A Embodiment-A through FIG. 11A Embodiment-E axially translates the camshaft-1511 to remove the tubing assembly compression. Camshaft-1511 axial-translation, initiated by the lever 307 and its mechanism, moves the contact of finger-set-1 312 and finger-set-2 313 from the cam-profile 513 to the cam-taper 514. At a given portion of the cam-taper 514, all fingers lose contact with the tubing, resulting in no compression, allowing disassembly of the tubing and the cassette utilized. Secondly, the procedure for removing and installing new tubing and cassette-F1 1201 for FIG. 12A Embodiment-F1 follows. Pushing the protrusion of tube-hold-2 1209 allows cassette-F1 1201 to be removed or installed, and it compresses the tubing-F1 1203 and tubing-F2 1204 to their proper operating mode. Unlike the other embodiments, FIG. 12A Embodiment-F1 through FIG. 14B Embodiment-F3 entails that the tubing assembly and the cassette be installed and uninstalled separately. Tube-hold-2 1209 positions tubing-F1 1203 and tubing-F2 1204, which is the tube-seat for the tubing. FIG. 15A Embodiment-G1 through FIG. 16A Embodiment-G4 operate the same as FIG. 12A Embodiment-A through FIG. 14B Embodiment-F3, with the tube-hold and the cassette combined into cassette utilized.

Tube-hold-1, utilized in FIG. 3A Embodiment-A through FIG. 11A Embodiment E, provides an option to guide a variety of tubes within cassettes and helps alignment with the mating pump-assembly. Tube-hold-2 1209 is utilized and required in FIG. 12A Embodiment-F1 to orient the tubing and perform as the tube-seat, yielding continuous flow output Qout. The term tube-seat, the tube seating surface function of all embodiments, varies in location, from base-1 or base-2 of three embodiments and the cassette for the other eight embodiments.

The term tube-seat is the cavity-opening of the internal surface of cassette-B 705, as shown in FIG. 7C. The tube-seat of cassette-D 903 is its internal diameter, as shown in FIG. 9C. FIG. 3A Embodiment-A through section B-B of FIG. 6A utilizes the internal surface of annular-flange-1403 of base-1 302 as the tube-seat. FIG. 8A Embodiment-C also utilizes annular-flange-1403 of base-1 302 as its tube-seat.

FIG. 8B shows that the tubing-assembly-2 803 isn't touching the internal diameter of cassette-C. This diameter mates with the external diameter of annular-flange-1403. FIG. 11A Embodiment-E also utilizes annular-flange-1 as its tube-seat. FIG. 12A Embodiment-F1 utilizes tube-hold-2 1209 as its tube-seat for tubing-F1 1203 and tubing-F2 1204. Similarly, FIG. 14A Embodiment-F2 and FIG. 14B Embodiment-F3 utilize their tube-hold parts as the tube-seat. FIG. 15A Embodiment-G1, FIG. 15C Embodiment-G2, and FIG. 15D Embodiment-G3 all utilize their cassettes as the tube-seat. The tube-hold part features of the F-embodiments, combined into the design of their cassettes, are functionally the same as the G-embodiments. The cassette, independent of the implementation, houses the tubing-assembly. The tubing-assembly includes connectors to the inputs and outputs of the pump and combines the parallel set of tube-sections. The input to the pump corresponds with the input of the tube-sections. Similarly, the pump's output corresponds with the output of the parallel tube-sections. Clockwise rotation of the camshaft corresponds with the pump's input and outputs as described in all embodiments. Counterclockwise rotation of the camshaft, typically in non-medical applications, flips the pump's inputs and outputs, effectively changing the flow direction wherein the inputs become the outputs, and the outputs become the inputs.

Sleeve-1 311, sleeve-2 904, sleeve-3 1206, and sleeve-4 1407 align all fingers to interface with the tubing and tube-seat, depending on the embodiment utilized. This alignment is the plane of action of the sleeves and fingers, including a given embodiment's cam-profile. These single-piece sleeves provide the phasing of the embodiment utilized. Fine-tuning of the phasing, utilized by a multiple-part sleeve (not shown), is accomplished with finger-set-1312 contained in one sleeve and finger-set-2 313 in a second sleeve (not shown). Therefore, the phasing and other angles are approximate as designed or with tolerances utilized in manufacturing components. For example, a phasing of 180-degrees would operate properly at 178-degrees. The finger styles utilized include finger-5a 601, shown in FIG. 6D, and finger-5c 902, shown in FIG. 17A through FIG. 17C. Additional embodiments can utilize a variety of other shapes and combinations of these shapes. The plane of action for FIG. 3A Embodiment-A through FIG. 11A Embodiment-E changes the axial location of the camshaft from the cam-profile 513 to the cam-taper 514. The cam-taper 514 blends from the cam-profile 513 surface, decreasing radially, allowing the fingers to remove the tubing compression gradually.

The twelve embodiments yield continuous flow output Qout as a function of its camshaft rotation, wherein the volume of fluid output Vout is proportional to the camshaft rotation. The gearing and the motor have a linear relationship between the electrical input signal to the camshaft rotation. The twelve embodiments, therefore, yield continuous flow output Qout as a function of the electrical input signal, wherein the volume of fluid output Vout is proportional to the electrical input signal. The rotary input could be as simple as a hand-crank with manual input to control the camshaft rotation directly. Other embodiments are possible, including an attachable power supply. The tube-hold and cassette utilized in a given embodiment can be re-used and recycled.

Medical applications typically control the rotation of the camshaft in one rotary direction to avoid back-flow and other potential problems involving the patient. Non-medical and some medical applications utilize FIG. 11A Embodiment-E, FIG. 12A Embodiment-F1, and FIG. 15A Embodiment-G1, providing two-way fluid flow. Mixing fluids, as well as other non-medical applications utilizing these bidirectional embodiments, can be employed. All the embodiments employ a tubing-assembly with an inlet and outlet. The direction of the camshaft rotation can effectively change the nomenclature of the inlet and the outlet to change polarity. The physical size of a pump varies depending on implementation, including the rotary input means for the transmission of energy, as discussed. A mobile application, or a mobile app, can supplement or remove the need for a screen within a pump. The mobile app could also share the control logic of the pump operation. FIG. 16A Embodiment-G4 utilizes a mobile app and smaller batteries, yielding the embodiment's smaller physical envelope. A camshaft controlled manually with an attached hand-crank would not require the motor and other components, including batteries and electronics, simplifying the pump-assembly and the pump itself. All of the embodiments provide the advantage of continuous-flow output as a function of the input. In contrast, prior-art peristaltic pumps do not provide continuous flow output as a function of rotation and can, in some instances, create safety concerns for the patient.

I claim:

1. A pump for delivering continuous fluid flow comprising:
    a. a pump-assembly including a bore and a rotary input means for the transmission of energy;
    b. a camshaft, guided in the bore of the pump-assembly, with a proximal cam and a distal cam, wherein the distal cam is at a predetermined angle from the proximal cam of which both cams have the same cam-profile of a regular polygon with equal radii corners;
    c. a sleeve with a central hole, mounted in and aligned with the bore of the pump-assembly, with a proximal set and a distal set of a plurality of equal angular spaced holes radiating from the central hole wherein the phase-angle between the two sets of holes is predetermined;
    d. a plurality of fingers aligned within the holes of the sleeve;
    e. a cassette with an internal void combined with an access-hole, mounted and aligned to the pump-assembly and its bore;
    f. a tubing-assembly, connected within the cassette, with a proximal tube-section and a distal tube-section wherein each tube-section has an inlet and an outlet corresponding to an inlet and outlet of the tubing-assembly;
    whereby the rotary input rotates the camshaft in the bore of the pump-assembly such that the cam-profile of each of the camshaft's cams urges the fingers' proximal ends to slidably translate within the two sets of holes of the sleeve, wherein the fingers' distal ends cyclically compress each of the tube-sections, sandwiched between the cassette's tube-seat and the fingers, such that each tube-section draws in fluid from the tubing-assembly's inlet and delivers the combined flow output from the tube-sections' outlets yielding continuous fluid-flow out of the outlet of the tubing-assembly as a function of the camshaft rotation.

2. The pump of claim 1 further comprising an infusion-bag,
    wherein the infusion-bag, contained in the internal void of the cassette, provides the inlet fluid source for both of the tube-sections of the device.

3. The pump of claim 1, wherein
the distal cam is approximately 60-degrees from the proximal cam and each cam has a cam-profile of an equilateral triangle with equal radii corners; and
the phase-angle between the two sets of holes is approximately 0-degrees.

4. The pump of claim 1, wherein
the distal cam orientation is approximately 0-degrees from the proximal cam wherein each cam has a cam-profile of an equilateral triangle with equal radii corners; and
the phrase-angle between the two sets of holes is approximately 60-degrees.

5. A pump for delivering continuous fluid-flow comprising:
   a. a pump-assembly including a bore and a rotary input means for the transmission of energy;
   b. a camshaft, guided in the bore of the pump-assembly, with a single cam with a cam-profile of a regular polygon with equal radii corners;
   c. a sleeve with a central hole, mounted in and aligned with the bore of the pump-assembly, containing two sets of a plurality of equal angular spaced holes radiating from the central hole, wherein the phase-angle between the two sets of holes is predetermined;
   d. a plurality of fingers guided within the holes of the sleeve;
   e. a cassette with an internal void combined with an access-hole, mounted and aligned to the pump-assembly and its bore;
   f. a tubing-assembly, connected within the cassette, including two tube-sections wherein each tube-section has an inlet and an outlet corresponding to an inlet and outlet of the tubing-assembly;
whereby the rotary input rotates the camshaft in the bore of the pump-assembly such that the camshaft's cam-profile urges the fingers' proximal ends to slidably translate within the two sets of holes of the sleeve, wherein the fingers' distal ends cyclically compress each of the tube-sections, sandwiched between the tube-seat and the fingers, such that each tube-section draws in fluid from the tubing-assembly's inlet and delivers the combined flow output from the tube-sections' outlets yielding continuous fluid-flow out of the outlet of the tubing-assembly as a function of the camshaft rotation.

6. The pump of claim 5 further comprising an infusion-bag
wherein the infusion-bag, contained in the internal void of the cassette, provides the inlet fluid source for both of the tube-sections of the device.

7. The pump of claim 5, wherein
the camshaft's cam-profile is an equilateral triangle with equal radii corners; and
the phrase-angle between the two sets of holes is approximately 180-degrees.

8. The pump of claim 5 further comprising a tube-hold,
wherein the tube-hold contained within the cassette orients both tube-sections to align with the camshaft's cam-profile and both sets of fingers.

9. The pump of claim 5, wherein
each finger's proximal end is smaller than its distal end with a groove situated between each finger's proximal and distal end; and
wherein a counterbore opening at a distal end of each of the holes is larger than an opening at a proximal end of the associated hole;
the pump further comprising:
   a spring-retainer attached to the groove of each finger;
   a spring-stop attached to a distal end of each counterbore opening; and
   a compression spring, mated to each spring-stop and each spring-retainer; wherein the force of the compression spring urges the associated finger to maintain contact with the cam of the camshaft.

* * * * *